US011406392B2

(12) United States Patent
Karg

(10) Patent No.: US 11,406,392 B2
(45) Date of Patent: Aug. 9, 2022

(54) ANEURYSM OCCLUDING DEVICE FOR USE WITH COAGULATING AGENTS

(71) Applicant: DePuy Synthes Products, Inc., Raynham, MA (US)

(72) Inventor: Dillon Karg, Raynham, MA (US)

(73) Assignee: DePuy Synthes Products, Inc., Raynham, MA (US)

( * ) Notice: Subject to any disclaimer, the term of this patent is extended or adjusted under 35 U.S.C. 154(b) by 83 days.

(21) Appl. No.: 16/218,129

(22) Filed: Dec. 12, 2018

(65) Prior Publication Data

US 2020/0187950 A1 Jun. 18, 2020

(51) Int. Cl.
*A61B 17/12* (2006.01)
*A61B 17/00* (2006.01)

(52) U.S. Cl.
CPC .... *A61B 17/12113* (2013.01); *A61B 17/1215* (2013.01); *A61B 17/12186* (2013.01); *A61B 17/12136* (2013.01); *A61B 2017/00867* (2013.01); *A61B 2017/1205* (2013.01)

(58) Field of Classification Search
None
See application file for complete search history.

(56) References Cited

U.S. PATENT DOCUMENTS

| 2,849,002 | A | 8/1958 | Oddo |
| 3,480,017 | A | 11/1969 | Shute |
| 4,085,757 | A | 4/1978 | Pevsner |
| 4,282,875 | A | 4/1981 | Serbinenko et al. |
| 4,364,392 | A | 12/1982 | Strother et al. |
| 4,395,806 | A | 8/1983 | Wonder et al. |
| 4,517,979 | A | 5/1985 | Pecenka |
| 4,545,367 | A | 10/1985 | Tucci |
| 4,836,204 | A | 6/1989 | Landymore et al. |
| 4,991,602 | A | 2/1991 | Amplatz et al. |
| 5,002,556 | A | 3/1991 | Ishida et al. |
| 5,025,060 | A | 6/1991 | Yabuta et al. |

(Continued)

FOREIGN PATENT DOCUMENTS

| CA | 2395796 A1 | 7/2001 |
| CA | 2 431 594 A1 | 9/2002 |

(Continued)

OTHER PUBLICATIONS

Extended European Search Report issued in corresponding European Patent Application No. 19 21 5277 dated May 12, 2020.

(Continued)

*Primary Examiner* — Shaun L David
(74) *Attorney, Agent, or Firm* — Troutman Pepper Hamilton Sanders LLP

(57) ABSTRACT

Devices can generally include a fan portion for occluding an aneurysm neck, a channel orifice opening in the fan portion, and an agent channel for delivering a coagulating agent through the orifice into the aneurysm. Devices can be delivered through a catheter to the aneurysm, the fan portion can expand to occlude the aneurysm neck, and coagulating agent can be injected into the aneurysm. During injection of the coagulating agent, the fan portion can inhibit the coagulating agent from exiting the aneurysm. After injection of the coagulation agent, the fan portion can collapse and the device can be extracted from the patient.

12 Claims, 11 Drawing Sheets

(56) References Cited

U.S. PATENT DOCUMENTS

| | | |
|---|---|---|
| 5,065,772 A | 11/1991 | Cox, Jr. |
| 5,067,489 A | 11/1991 | Lind |
| 5,122,136 A | 6/1992 | Guglielmi et al. |
| 5,192,301 A | 3/1993 | Kamiya et al. |
| 5,261,916 A | 11/1993 | Engelson |
| 5,304,195 A | 4/1994 | Twyford, Jr. et al. |
| 5,334,210 A | 8/1994 | Gianturco |
| 5,350,397 A | 9/1994 | Palermo |
| 5,423,829 A | 6/1995 | Pham et al. |
| 5,624,449 A | 4/1997 | Pham et al. |
| 5,645,558 A | 7/1997 | Horton |
| 5,733,294 A | 3/1998 | Forber et al. |
| 5,916,235 A | 6/1999 | Guglielmi |
| 5,891,128 A | 7/1999 | Chin et al. |
| 5,928,260 A * | 7/1999 | Chin .............. A61B 17/12022 604/107 |
| 5,935,148 A | 8/1999 | Villar |
| 5,941,249 A | 8/1999 | Maynard |
| 5,951,599 A | 9/1999 | McCrory |
| 5,964,797 A | 10/1999 | Ho |
| 6,007,573 A | 12/1999 | Wallace et al. |
| 6,024,756 A | 2/2000 | Pham |
| 6,036,720 A | 3/2000 | Abrams |
| 6,063,070 A | 5/2000 | Eder |
| 6,063,100 A | 5/2000 | Diaz et al. |
| 6,063,104 A | 5/2000 | Villar |
| 6,080,191 A | 6/2000 | Thaler |
| 6,086,577 A | 7/2000 | Ken et al. |
| 6,096,021 A | 8/2000 | Helm et al. |
| 6,113,609 A | 9/2000 | Adams |
| 6,123,714 A | 9/2000 | Gia et al. |
| 6,168,615 B1 | 1/2001 | Ken |
| 6,168,622 B1 | 1/2001 | Mazzocchi |
| 6,193,708 B1 | 2/2001 | Ken et al. |
| 6,221,086 B1 | 4/2001 | Forber |
| 6,270,515 B1 | 8/2001 | Linden et al. |
| 6,315,787 B1 | 11/2001 | Tsugita et al. |
| 6,331,184 B1 | 12/2001 | Abrams |
| 6,334,048 B1 | 12/2001 | Edvardsson et al. |
| 6,346,117 B1 | 2/2002 | Greenhalgh |
| 6,350,270 B1 | 2/2002 | Roue |
| 6,375,606 B1 | 4/2002 | Garbaldi et al. |
| 6,375,668 B1 | 4/2002 | Gifford |
| 6,379,329 B1 | 4/2002 | Naglreiter et al. |
| 6,391,037 B1 | 5/2002 | Greenhalgh |
| 6,419,686 B1 | 7/2002 | McLeod et al. |
| 6,428,558 B1 | 8/2002 | Jones |
| 6,454,780 B1 | 9/2002 | Wallace |
| 6,463,317 B1 | 10/2002 | Kucharczyk et al. |
| 6,506,204 B2 | 1/2003 | Mazzocchi |
| 6,527,919 B1 | 3/2003 | Roth |
| 6,547,804 B2 | 4/2003 | Porter et al. |
| 6,551,303 B1 | 4/2003 | Van Tassel et al. |
| 6,569,179 B2 | 5/2003 | Teoh |
| 6,569,190 B2 | 5/2003 | Whalen, II et al. |
| 6,572,628 B2 | 6/2003 | Dominguez |
| 6,589,230 B2 | 7/2003 | Gia et al. |
| 6,589,256 B2 | 7/2003 | Forber |
| 6,605,102 B1 | 8/2003 | Mazzocchi et al. |
| 6,620,152 B2 | 9/2003 | Guglielmi |
| 6,669,719 B2 | 12/2003 | Wallace et al. |
| 6,689,159 B2 | 2/2004 | Lau et al. |
| 6,746,468 B1 | 6/2004 | Sepetka |
| 6,780,196 B2 | 8/2004 | Chin et al. |
| 6,802,851 B2 | 10/2004 | Jones |
| 6,811,560 B2 | 11/2004 | Jones |
| 6,833,003 B2 | 12/2004 | Jones et al. |
| 6,846,316 B2 | 1/2005 | Abrams |
| 6,849,081 B2 | 2/2005 | Sepetka et al. |
| 6,855,154 B2 | 2/2005 | Abdel-Gawwad |
| 6,949,116 B2 | 9/2005 | Solymar et al. |
| 6,964,657 B2 | 11/2005 | Cragg et al. |
| 6,964,671 B2 | 11/2005 | Cheng |
| 6,994,711 B2 | 2/2006 | Hieshima et al. |
| 7,044,134 B2 | 5/2006 | Khairkhahan et al. |
| 7,083,632 B2 | 8/2006 | Avellanet |
| 7,093,527 B2 | 8/2006 | Rapaport et al. |
| 7,128,736 B1 | 10/2006 | Abrams et al. |
| 7,152,605 B2 | 12/2006 | Khairkhahan et al. |
| 7,153,323 B1 | 12/2006 | Teoh |
| 7,195,636 B2 | 3/2007 | Avellanet et al. |
| 7,229,454 B2 | 6/2007 | Tran et al. |
| 7,229,461 B2 | 6/2007 | Chin et al. |
| 7,309,345 B2 | 12/2007 | Wallace |
| 7,371,249 B2 | 5/2008 | Douk et al. |
| 7,410,482 B2 | 8/2008 | Murphy et al. |
| 7,572,288 B2 | 8/2009 | Cox |
| 7,597,704 B2 | 10/2009 | Frazier et al. |
| 7,608,088 B2 | 10/2009 | Jones |
| 7,695,488 B2 | 4/2010 | Berenstein et al. |
| 7,713,264 B2 | 5/2010 | Murphy |
| 7,744,652 B2 | 6/2010 | Morsi |
| 7,892,248 B2 | 2/2011 | Tran |
| 7,985,238 B2 | 7/2011 | Balgobin et al. |
| RE42,758 E | 9/2011 | Ken |
| 8,016,852 B2 | 9/2011 | Ho |
| 8,021,416 B2 | 9/2011 | Abrams |
| 8,025,668 B2 | 9/2011 | McCartney |
| 8,034,061 B2 | 10/2011 | Amplatz et al. |
| 8,048,145 B2 | 11/2011 | Evans et al. |
| 8,062,325 B2 | 11/2011 | Mitelberg et al. |
| 8,075,585 B2 | 12/2011 | Lee et al. |
| 8,142,456 B2 | 3/2012 | Rosqueta et al. |
| 8,221,483 B2 | 7/2012 | Ford et al. |
| 8,261,648 B1 | 9/2012 | Marchand et al. |
| 8,267,923 B2 | 9/2012 | Murphy |
| 8,361,106 B2 | 1/2013 | Solar et al. |
| 8,361,138 B2 | 1/2013 | Adams |
| 8,372,114 B2 | 2/2013 | Hines |
| 8,398,671 B2 | 3/2013 | Chen |
| 8,430,012 B1 | 4/2013 | Marchand |
| 8,454,633 B2 | 6/2013 | Amplatz et al. |
| 8,523,897 B2 | 9/2013 | van der Burg et al. |
| 8,523,902 B2 | 9/2013 | Heaven et al. |
| 8,551,132 B2 | 10/2013 | Eskridge et al. |
| 8,777,974 B2 | 7/2014 | Amplatz et al. |
| 8,900,304 B1 | 12/2014 | Alobaid |
| 8,992,568 B2 | 3/2015 | Duggal et al. |
| 8,998,947 B2 | 3/2015 | Aboytes et al. |
| 8,974,512 B2 | 4/2015 | Aboytes et al. |
| 9,055,948 B2 | 6/2015 | Jaeger et al. |
| 9,107,670 B2 | 8/2015 | Hannes et al. |
| 9,161,758 B2 | 10/2015 | Figulla et al. |
| 9,232,992 B2 | 1/2016 | Heidner et al. |
| 9,259,337 B2 | 2/2016 | Cox et al. |
| 9,314,326 B2 | 4/2016 | Wallace et al. |
| 9,351,715 B2 | 5/2016 | Mach |
| 9,414,842 B2 | 8/2016 | Glimsdale et al. |
| 9,526,813 B2 | 12/2016 | Cohn et al. |
| 9,532,792 B2 | 1/2017 | Galdonik et al. |
| 9,532,873 B2 | 1/2017 | Kelley |
| 9,533,344 B2 | 1/2017 | Monetti et al. |
| 9,539,011 B2 | 1/2017 | Chen et al. |
| 9,539,022 B2 | 1/2017 | Bowman |
| 9,539,122 B2 | 1/2017 | Burke et al. |
| 9,539,382 B2 | 1/2017 | Nelson |
| 9,549,830 B2 | 1/2017 | Bruszewski et al. |
| 9,554,805 B2 | 1/2017 | Tompkins et al. |
| 9,561,096 B2 | 2/2017 | Kim et al. |
| 9,561,125 B2 | 2/2017 | Bowman et al. |
| 9,572,982 B2 | 2/2017 | Burnes et al. |
| 9,579,104 B2 | 2/2017 | Beckham et al. |
| 9,579,484 B2 | 2/2017 | Barnell |
| 9,585,642 B2 | 3/2017 | Dinsmoor et al. |
| 9,585,669 B2 | 3/2017 | Becking et al. |
| 9,615,832 B2 | 4/2017 | Bose et al. |
| 9,615,951 B2 | 4/2017 | Bennett et al. |
| 9,622,753 B2 | 4/2017 | Cox |
| 9,629,635 B2 | 4/2017 | Hewitt et al. |
| 9,636,115 B2 | 5/2017 | Henry et al. |
| 9,636,439 B2 | 5/2017 | Chu et al. |
| 9,642,675 B2 | 5/2017 | Werneth et al. |
| 9,655,633 B2 | 5/2017 | Leynov et al. |
| 9,655,645 B2 | 5/2017 | Staunton |

(56) References Cited

U.S. PATENT DOCUMENTS

| | | | |
|---|---|---|---|
| 9,655,989 B2 | 5/2017 | Cruise et al. |
| 9,662,129 B2 | 5/2017 | Galdonik et al. |
| 9,662,238 B2 | 5/2017 | Dwork et al. |
| 9,662,425 B2 | 5/2017 | Lilja et al. |
| 9,668,898 B2 | 6/2017 | Wong |
| 9,675,477 B2 | 6/2017 | Thompson |
| 9,675,782 B2 | 6/2017 | Connolly |
| 9,676,022 B2 | 6/2017 | Ensign et al. |
| 9,681,861 B2 | 6/2017 | Heisel et al. |
| 9,692,557 B2 | 6/2017 | Murphy |
| 9,693,852 B2 | 7/2017 | Lam et al. |
| 9,700,262 B2 | 7/2017 | Janik et al. |
| 9,700,399 B2 | 7/2017 | Acosta-Acevedo |
| 9,717,421 B2 | 8/2017 | Griswold et al. |
| 9,717,500 B2 | 8/2017 | Tieu et al. |
| 9,717,502 B2 | 8/2017 | Teoh et al. |
| 9,724,103 B2 | 8/2017 | Cruise et al. |
| 9,724,526 B2 | 8/2017 | Strother et al. |
| 9,750,565 B2 | 9/2017 | Bloom et al. |
| 9,757,260 B2 | 9/2017 | Greenan |
| 9,764,111 B2 | 9/2017 | Gulachenski |
| 9,770,251 B2 | 9/2017 | Bowman |
| 9,770,577 B2 | 9/2017 | Li et al. |
| 9,775,621 B2 | 10/2017 | Tompkins et al. |
| 9,775,706 B2 | 10/2017 | Peterson et al. |
| 9,775,732 B2 | 10/2017 | Khenansho |
| 9,788,800 B2 | 10/2017 | Mayoras, Jr. |
| 9,795,391 B2 | 10/2017 | Saatchi et al. |
| 9,801,980 B2 | 10/2017 | Karino et al. |
| 9,808,599 B2 | 11/2017 | Bowman et al. |
| 9,833,252 B2 | 12/2017 | Sepetka |
| 9,833,604 B2 | 12/2017 | Lam et al. |
| 9,833,625 B2 | 12/2017 | Waldhauser et al. |
| 9,918,720 B2 | 3/2018 | Marchand et al. |
| 9,955,976 B2 | 5/2018 | Hewitt et al. |
| 10,004,510 B2 | 6/2018 | Gerberding |
| 10,130,372 B2 | 11/2018 | Griffin |
| 10,307,148 B2 | 6/2019 | Heisel et al. |
| 10,327,781 B2 | 6/2019 | Divino et al. |
| 10,342,546 B2 | 7/2019 | Sepetka et al. |
| 10,517,604 B2 | 12/2019 | Bowman et al. |
| 10,653,425 B1 | 5/2020 | Gorochow et al. |
| 10,716,573 B2 | 7/2020 | Connor |
| 2002/0068974 A1 | 6/2002 | Kuslich et al. |
| 2002/0082638 A1 | 6/2002 | Porter et al. |
| 2002/0143349 A1 | 10/2002 | Gifford, III et al. |
| 2002/0147497 A1 | 10/2002 | Belef et al. |
| 2002/0165582 A1* | 11/2002 | Porter ............... A61B 17/12195 606/213 |
| 2002/0188314 A1 | 12/2002 | Anderson et al. |
| 2003/0028209 A1* | 2/2003 | Teoh ................ A61B 17/12172 606/191 |
| 2003/0120337 A1 | 6/2003 | Van Tassel et al. |
| 2003/0171739 A1 | 9/2003 | Murphy |
| 2003/0176884 A1 | 9/2003 | Berrada et al. |
| 2003/0181927 A1* | 9/2003 | Wallace ........... A61B 17/12022 606/151 |
| 2003/0181945 A1 | 9/2003 | Opolski |
| 2003/0195553 A1 | 10/2003 | Wallace |
| 2003/0216772 A1 | 11/2003 | Konya |
| 2004/0034366 A1 | 2/2004 | van der Burg et al. |
| 2004/0034386 A1 | 2/2004 | Fulton et al. |
| 2004/0044391 A1 | 3/2004 | Porter |
| 2004/0087998 A1 | 5/2004 | Lee et al. |
| 2004/0098027 A1 | 5/2004 | Teoh et al. |
| 2004/0127935 A1 | 7/2004 | Van Tassel et al. |
| 2004/0133222 A1 | 7/2004 | Tran et al. |
| 2004/0153120 A1 | 8/2004 | Seifert et al. |
| 2004/0172056 A1* | 9/2004 | Guterman ........ A61B 17/12118 606/200 |
| 2004/0193206 A1* | 9/2004 | Gerberding ...... A61B 17/12118 606/200 |
| 2004/0210297 A1 | 10/2004 | Lin et al. |
| 2004/0254594 A1 | 12/2004 | Alfaro |
| 2005/0021016 A1 | 1/2005 | Malecki et al. |
| 2005/0021072 A1 | 1/2005 | Wallace |
| 2005/0159771 A1 | 7/2005 | Petersen |
| 2005/0177103 A1 | 8/2005 | Hunter et al. |
| 2005/0251200 A1 | 11/2005 | Porter |
| 2006/0052816 A1 | 3/2006 | Bates et al. |
| 2006/0058735 A1 | 3/2006 | Lesh |
| 2006/0064151 A1 | 3/2006 | Guterman et al. |
| 2006/0106421 A1 | 5/2006 | Teoh |
| 2006/0155323 A1 | 7/2006 | Porter et al. |
| 2006/0155367 A1 | 7/2006 | Hines |
| 2006/0167494 A1 | 7/2006 | Suddaby |
| 2006/0247572 A1 | 11/2006 | McCartney |
| 2007/0088387 A1 | 4/2007 | Eskridge et al. |
| 2007/0106311 A1 | 5/2007 | Wallace et al. |
| 2007/0208376 A1 | 6/2007 | Meng |
| 2007/0162071 A1 | 7/2007 | Burkett et al. |
| 2007/0167876 A1 | 7/2007 | Euteneuer et al. |
| 2007/0173928 A1 | 7/2007 | Morsi |
| 2007/0186933 A1 | 8/2007 | Domingo |
| 2007/0191884 A1 | 8/2007 | Eskridge et al. |
| 2007/0233188 A1 | 10/2007 | Hunt et al. |
| 2007/0265656 A1 | 11/2007 | Amplatz et al. |
| 2007/0288083 A1 | 12/2007 | Hines |
| 2008/0097495 A1 | 4/2008 | Feller, III et al. |
| 2008/0103505 A1 | 5/2008 | Fransen |
| 2008/0119886 A1 | 5/2008 | Greenhalgh et al. |
| 2008/0281350 A1 | 11/2008 | Sepetka et al. |
| 2009/0036877 A1 | 2/2009 | Nardone et al. |
| 2009/0062841 A1 | 3/2009 | Amplatz et al. |
| 2009/0099647 A1 | 4/2009 | Glimsdale |
| 2009/0227983 A1 | 9/2009 | Griffin et al. |
| 2009/0281557 A1 | 11/2009 | Sander et al. |
| 2009/0287291 A1 | 11/2009 | Becking et al. |
| 2009/0287297 A1 | 11/2009 | Cox |
| 2009/0318941 A1 | 12/2009 | Sepetka |
| 2010/0023046 A1 | 1/2010 | Heidner et al. |
| 2010/0023048 A1 | 1/2010 | Mach |
| 2010/0063573 A1 | 3/2010 | Hijlkema |
| 2010/0063582 A1 | 3/2010 | Rudakov |
| 2010/0069948 A1 | 3/2010 | Veznedaroglu et al. |
| 2010/0168781 A1 | 7/2010 | Berenstein |
| 2010/0211156 A1 | 8/2010 | Linder et al. |
| 2010/0324649 A1 | 12/2010 | Mattsson et al. |
| 2011/0046658 A1 | 2/2011 | Conner et al. |
| 2011/0054519 A1 | 3/2011 | Neuss |
| 2011/0112588 A1 | 5/2011 | Linderman et al. |
| 2011/0137317 A1 | 6/2011 | O'Halloran et al. |
| 2011/0152993 A1 | 6/2011 | Marchand et al. |
| 2011/0196413 A1 | 8/2011 | Wallace |
| 2011/0319978 A1 | 12/2011 | Schaffer |
| 2012/0010644 A1 | 1/2012 | Sideris et al. |
| 2012/0071911 A1 | 3/2012 | Sadasivan |
| 2012/0165732 A1 | 6/2012 | Müller |
| 2012/0191123 A1 | 7/2012 | Brister et al. |
| 2012/0283768 A1 | 11/2012 | Cox et al. |
| 2012/0310270 A1 | 12/2012 | Murphy |
| 2012/0323267 A1 | 12/2012 | Ren |
| 2012/0330341 A1 | 12/2012 | Becking et al. |
| 2013/0035665 A1 | 2/2013 | Chu |
| 2013/0035712 A1 | 2/2013 | Theobald et al. |
| 2013/0066357 A1 | 3/2013 | Aboytes et al. |
| 2013/0079864 A1 | 3/2013 | Boden |
| 2013/0110066 A1 | 5/2013 | Sharma et al. |
| 2013/0204351 A1 | 8/2013 | Cox et al. |
| 2013/0211495 A1 | 8/2013 | Halden et al. |
| 2013/0261658 A1 | 10/2013 | Lorenzo et al. |
| 2013/0261730 A1 | 10/2013 | Bose et al. |
| 2013/0274863 A1 | 10/2013 | Cox et al. |
| 2013/0345738 A1 | 12/2013 | Eskridge |
| 2014/0005714 A1 | 1/2014 | Quick et al. |
| 2014/0012307 A1 | 1/2014 | Franano et al. |
| 2014/0012363 A1 | 1/2014 | Franano et al. |
| 2014/0018838 A1 | 1/2014 | Franano et al. |
| 2014/0135812 A1 | 5/2014 | Divino et al. |
| 2014/0200607 A1 | 7/2014 | Sepetka et al. |
| 2014/0257360 A1 | 9/2014 | Keillor |
| 2014/0257361 A1 | 9/2014 | Prom |
| 2014/0277013 A1 | 9/2014 | Sepetka et al. |

(56) References Cited

U.S. PATENT DOCUMENTS

| | | |
|---|---|---|
| 2014/0358178 A1 | 12/2014 | Hewitt et al. |
| 2015/0057703 A1 | 2/2015 | Ryan et al. |
| 2015/0209050 A1 | 7/2015 | Aboytes et al. |
| 2015/0272589 A1 | 10/2015 | Lorenzo |
| 2015/0313605 A1* | 11/2015 | Griffin .................. A61B 90/39 606/200 |
| 2015/0342613 A1 | 12/2015 | Aboytes et al. |
| 2015/0374483 A1 | 12/2015 | Janardhan et al. |
| 2016/0022445 A1 | 1/2016 | Ruvalcaba et al. |
| 2016/0030050 A1 | 2/2016 | Franano et al. |
| 2016/0192912 A1 | 7/2016 | Kassab et al. |
| 2016/0249934 A1 | 9/2016 | Hewitt et al. |
| 2016/0249935 A1 | 9/2016 | Hewitt et al. |
| 2017/0007264 A1 | 1/2017 | Cruise et al. |
| 2017/0007265 A1 | 1/2017 | Guo et al. |
| 2017/0020670 A1 | 1/2017 | Murray et al. |
| 2017/0020700 A1 | 1/2017 | Bienvenu et al. |
| 2017/0027640 A1 | 2/2017 | Kunis et al. |
| 2017/0027692 A1 | 2/2017 | Bonhoeffer et al. |
| 2017/0027725 A1 | 2/2017 | Argentine |
| 2017/0035436 A1 | 2/2017 | Morita |
| 2017/0035567 A1 | 2/2017 | Duffy |
| 2017/0042548 A1 | 2/2017 | Lam |
| 2017/0049596 A1 | 2/2017 | Schabert |
| 2017/0071737 A1 | 3/2017 | Kelley |
| 2017/0072452 A1 | 3/2017 | Monetti et al. |
| 2017/0079661 A1 | 3/2017 | Bardsley et al. |
| 2017/0079662 A1 | 3/2017 | Rhee et al. |
| 2017/0079671 A1 | 3/2017 | Morero et al. |
| 2017/0079680 A1 | 3/2017 | Bowman |
| 2017/0079717 A1 | 3/2017 | Walsh et al. |
| 2017/0079766 A1 | 3/2017 | Wang et al. |
| 2017/0079767 A1 | 3/2017 | Leon-Yip |
| 2017/0079812 A1 | 3/2017 | Lam et al. |
| 2017/0079817 A1 | 3/2017 | Sepetka et al. |
| 2017/0079819 A1 | 3/2017 | Pung et al. |
| 2017/0079820 A1 | 3/2017 | Lam et al. |
| 2017/0086851 A1 | 3/2017 | Wallace et al. |
| 2017/0086996 A1 | 3/2017 | Peterson et al. |
| 2017/0095259 A1 | 4/2017 | Tompkins et al. |
| 2017/0100126 A1 | 4/2017 | Bowman et al. |
| 2017/0100141 A1 | 4/2017 | Morero et al. |
| 2017/0100143 A1 | 4/2017 | Granfield |
| 2017/0100183 A1 | 4/2017 | Iaizzo et al. |
| 2017/0113023 A1 | 4/2017 | Steingisser et al. |
| 2017/0114350 A1 | 4/2017 | dos Santos et al. |
| 2017/0147765 A1 | 5/2017 | Mehta |
| 2017/0151032 A1 | 6/2017 | Loisel |
| 2017/0165062 A1 | 6/2017 | Rothstein |
| 2017/0165065 A1 | 6/2017 | Rothstein et al. |
| 2017/0165454 A1 | 6/2017 | Tuohy et al. |
| 2017/0172581 A1 | 6/2017 | Bose et al. |
| 2017/0172766 A1 | 6/2017 | Vong et al. |
| 2017/0172772 A1 | 6/2017 | Khenansho |
| 2017/0189033 A1 | 7/2017 | Sepetka et al. |
| 2017/0189035 A1 | 7/2017 | Porter |
| 2017/0215902 A1 | 8/2017 | Leynov et al. |
| 2017/0216484 A1 | 8/2017 | Cruise et al. |
| 2017/0224350 A1 | 8/2017 | Shimizu et al. |
| 2017/0224355 A1 | 8/2017 | Bowman et al. |
| 2017/0224467 A1 | 8/2017 | Piccagli et al. |
| 2017/0224511 A1 | 8/2017 | Dwork et al. |
| 2017/0224953 A1 | 8/2017 | Tran et al. |
| 2017/0231749 A1 | 8/2017 | Perkins et al. |
| 2017/0252064 A1 | 9/2017 | Staunton |
| 2017/0265983 A1 | 9/2017 | Lam et al. |
| 2017/0281192 A1 | 10/2017 | Tieu et al. |
| 2017/0281331 A1 | 10/2017 | Perkins et al. |
| 2017/0281344 A1 | 10/2017 | Costello |
| 2017/0281909 A1 | 10/2017 | Northrop et al. |
| 2017/0281912 A1 | 10/2017 | Melder et al. |
| 2017/0290593 A1 | 10/2017 | Cruise et al. |
| 2017/0290654 A1 | 10/2017 | Sethna |
| 2017/0296324 A1 | 10/2017 | Argentine |
| 2017/0296325 A1 | 10/2017 | Marrocco et al. |
| 2017/0303939 A1 | 10/2017 | Greenhalgh et al. |
| 2017/0303942 A1 | 10/2017 | Greenhalgh et al. |
| 2017/0303947 A1 | 10/2017 | Greenhalgh et al. |
| 2017/0303948 A1 | 10/2017 | Wallace et al. |
| 2017/0304041 A1 | 10/2017 | Argentine |
| 2017/0304097 A1 | 10/2017 | Corwin et al. |
| 2017/0304595 A1 | 10/2017 | Nagasrinivasa et al. |
| 2017/0312109 A1 | 11/2017 | Le |
| 2017/0312484 A1 | 11/2017 | Shipley et al. |
| 2017/0316561 A1 | 11/2017 | Helm et al. |
| 2017/0319826 A1 | 11/2017 | Bowman et al. |
| 2017/0333228 A1 | 11/2017 | Orth et al. |
| 2017/0333236 A1 | 11/2017 | Greenan |
| 2017/0333678 A1 | 11/2017 | Bowman et al. |
| 2017/0340333 A1 | 11/2017 | Badruddin et al. |
| 2017/0340383 A1 | 11/2017 | Bloom et al. |
| 2017/0348014 A1 | 12/2017 | Wallace et al. |
| 2017/0348514 A1 | 12/2017 | Guyon et al. |
| 2018/0140305 A1 | 5/2018 | Connor |
| 2018/0153556 A1* | 6/2018 | Walzman ................ A61L 31/14 |
| 2018/0242979 A1 | 8/2018 | Lorenzo |
| 2018/0303531 A1* | 10/2018 | Sanders ............ A61B 17/8816 |
| 2018/0338767 A1 | 11/2018 | Dasnurkar et al. |
| 2019/0008522 A1 | 1/2019 | Lorenzo |
| 2019/0223878 A1 | 1/2019 | Lorenzo et al. |
| 2019/0110796 A1 | 4/2019 | Jayaraman |
| 2019/0142567 A1 | 5/2019 | Janardhan et al. |
| 2019/0192162 A1 | 6/2019 | Lorenzo |
| 2019/0192167 A1 | 6/2019 | Lorenzo |
| 2019/0192168 A1 | 6/2019 | Lorenzo |
| 2019/0223879 A1 | 7/2019 | Jayaraman |
| 2019/0223881 A1 | 9/2019 | Hewitt et al. |
| 2019/0328398 A1 | 10/2019 | Lorenzo |
| 2019/0357914 A1 | 11/2019 | Gorochow et al. |
| 2019/0365385 A1 | 12/2019 | Gorochow et al. |
| 2020/0069313 A1 | 3/2020 | Xu et al. |
| 2020/0268365 A1 | 8/2020 | Hebert et al. |

FOREIGN PATENT DOCUMENTS

| | | |
|---|---|---|
| CA | 2598048 A1 | 5/2008 |
| CN | 204 683 687 U | 7/2015 |
| DE | 102008015781 A1 | 10/2009 |
| DE | 102010053111 A1 | 6/2012 |
| DE | 102009058132 B4 | 7/2014 |
| DE | 10 2013 106031 A1 | 12/2014 |
| DE | 202008018523 U1 | 4/2015 |
| DE | 102011102955 B4 | 5/2018 |
| EP | 902704 B1 | 3/1999 |
| EP | 1054635 B1 | 11/2000 |
| EP | 1295563 A1 | 3/2003 |
| EP | 1441649 B1 | 8/2004 |
| EP | 1483009 B1 | 12/2004 |
| EP | 1527753 B1 | 5/2005 |
| EP | 1569565 B1 | 9/2005 |
| EP | 1574169 B1 | 9/2005 |
| EP | 1494619 B1 | 1/2006 |
| EP | 1633275 B1 | 3/2006 |
| EP | 1659988 B1 | 5/2006 |
| EP | 1725185 B1 | 11/2006 |
| EP | 1862122 A1 | 12/2007 |
| EP | 1923005 B1 | 5/2008 |
| EP | 2063791 B1 | 6/2009 |
| EP | 2134263 B1 | 12/2009 |
| EP | 2157937 B1 | 3/2010 |
| EP | 2266456 A1 | 12/2010 |
| EP | 2324775 B1 | 5/2011 |
| EP | 2367482 B1 | 9/2011 |
| EP | 2387951 B1 | 11/2011 |
| EP | 2460476 A2 | 6/2012 |
| EP | 2468349 A1 | 6/2012 |
| EP | 2543345 A1 | 1/2013 |
| EP | 2567663 A1 | 3/2013 |
| EP | 2617386 A1 | 7/2013 |
| EP | 2623039 A1 | 8/2013 |
| EP | 2647343 A2 | 10/2013 |
| EP | 2848211 A1 | 3/2015 |
| EP | 2854704 B1 | 4/2015 |
| EP | 2923674 B1 | 9/2015 |

(56) References Cited

FOREIGN PATENT DOCUMENTS

| | | |
|---|---|---|
| EP | 2926744 A1 | 10/2015 |
| EP | 3146916 A1 | 3/2017 |
| EP | 3501429 A1 | 6/2019 |
| EP | 3517055 A1 | 7/2019 |
| JP | H04-47415 U | 4/1992 |
| JP | H07-37200 U | 7/1995 |
| JP | 2006-509578 A | 3/2006 |
| JP | 2013-509972 A | 3/2013 |
| JP | 2013537069 A | 9/2013 |
| JP | 2014-522268 A | 9/2014 |
| JP | 2016-502925 A | 2/2015 |
| WO | WO 9641589 A1 | 12/1996 |
| WO | WO 9905977 A1 | 2/1999 |
| WO | WO 9908607 A1 | 2/1999 |
| WO | WO 9930640 A1 | 6/1999 |
| WO | WO 2003073961 A1 | 9/2003 |
| WO | WO 03/086240 A1 | 10/2003 |
| WO | WO 2005020822 A1 | 3/2005 |
| WO | WO 2005074814 A2 | 8/2005 |
| WO | WO 2005117718 A1 | 12/2005 |
| WO | WO 2006034149 A2 | 3/2006 |
| WO | WO 2006052322 A2 | 5/2006 |
| WO | 2007/076480 A2 | 7/2007 |
| WO | WO 2008150346 A1 | 12/2008 |
| WO | WO 2008151204 A1 | 12/2008 |
| WO | WO 2009048700 A1 | 4/2009 |
| WO | WO 2009105365 A1 | 8/2009 |
| WO | WO 2009132045 A2 | 10/2009 |
| WO | WO 2009135166 A2 | 11/2009 |
| WO | WO 2010030991 A1 | 3/2010 |
| WO | WO 2011057002 A2 | 5/2011 |
| WO | WO 2012032030 A1 | 3/2012 |
| WO | WO 2012099704 A2 | 7/2012 |
| WO | WO 2012099909 A2 | 7/2012 |
| WO | WO 2012113554 A1 | 8/2012 |
| WO | WO 2013016618 A2 | 1/2013 |
| WO | WO 2013025711 A1 | 2/2013 |
| WO | WO 2013109309 A1 | 7/2013 |
| WO | WO 2013159065 A1 | 10/2013 |
| WO | WO 2013162817 A1 | 10/2013 |
| WO | WO 2014029835 A1 | 2/2014 |
| WO | WO 2014078286 A1 | 5/2014 |
| WO | WO 2014110589 A1 | 7/2014 |
| WO | WO 2014137467 A1 | 9/2014 |
| WO | WO 2015073704 A1 | 5/2015 |
| WO | WO 2015160721 A1 | 10/2015 |
| WO | WO 2015166013 A1 | 11/2015 |
| WO | WO 2015171268 A2 | 11/2015 |
| WO | WO 2015184075 A1 | 12/2015 |
| WO | WO 2015187196 A1 | 12/2015 |
| WO | WO 2016044647 A2 | 3/2016 |
| WO | WO 2016107357 A1 | 7/2016 |
| WO | WO 2016137997 A1 | 9/2016 |
| WO | WO 2017/161283 A1 | 9/2017 |
| WO | WO 2018051187 A1 | 3/2018 |
| WO | WO 2019/038293 A1 | 2/2019 |
| WO | WO 2012/034135 A1 | 3/2021 |

OTHER PUBLICATIONS

Altes et al., Creation of Saccular Aneurysms in the Rabbit: A Model Suitable for Testing Endovascular Devices. AJR 2000; 174: 349-354.

Schaffer, Advanced Materials & Processes, Oct. 2002, pp. 51-54.

* cited by examiner

FIG. 2F
FIG. 3A
FIG. 3B
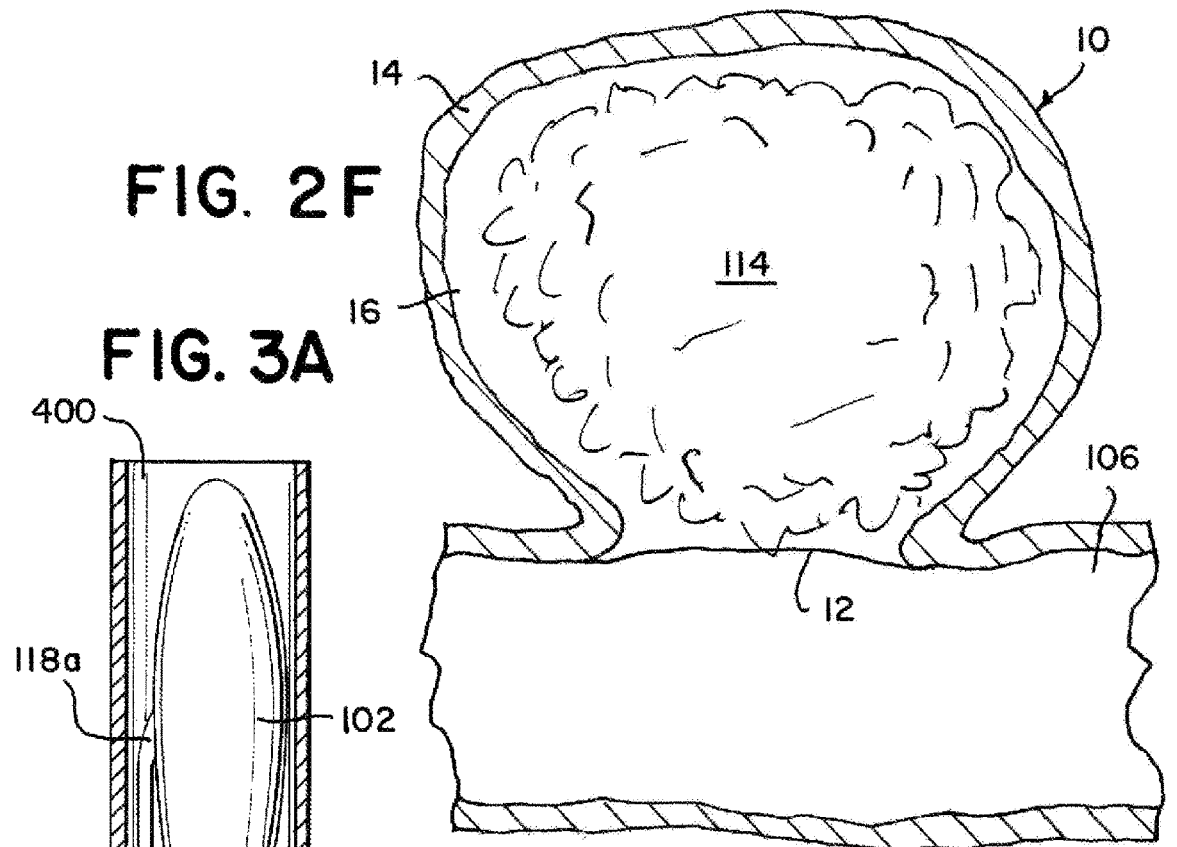
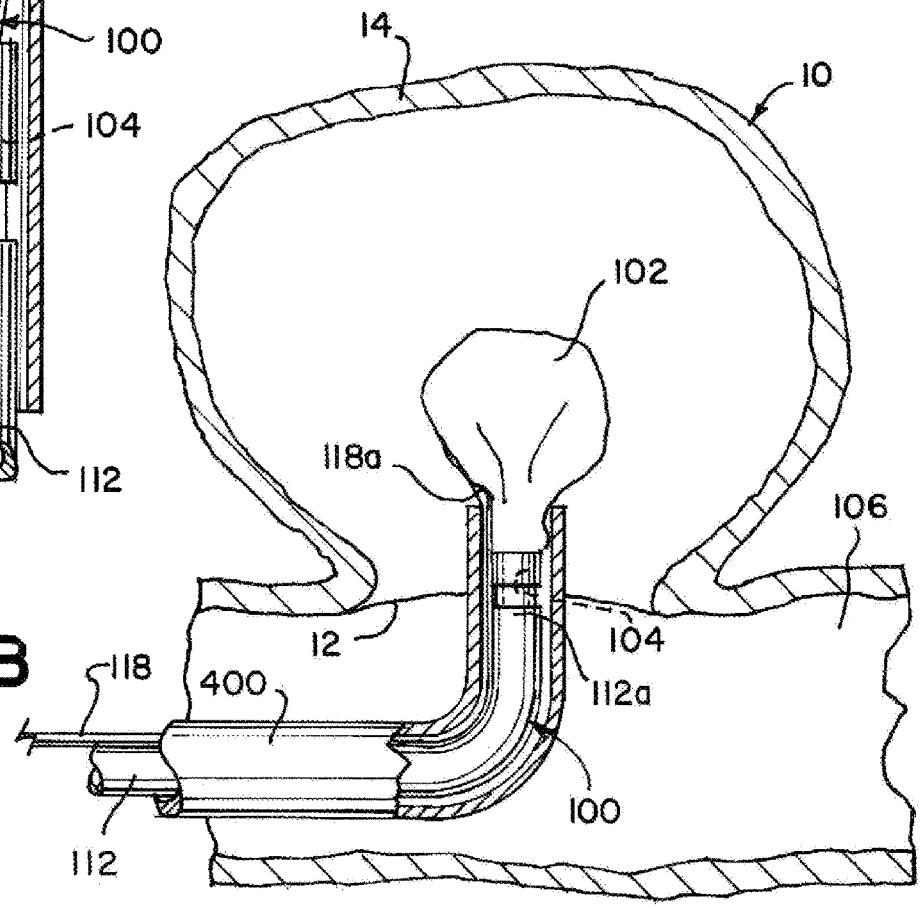

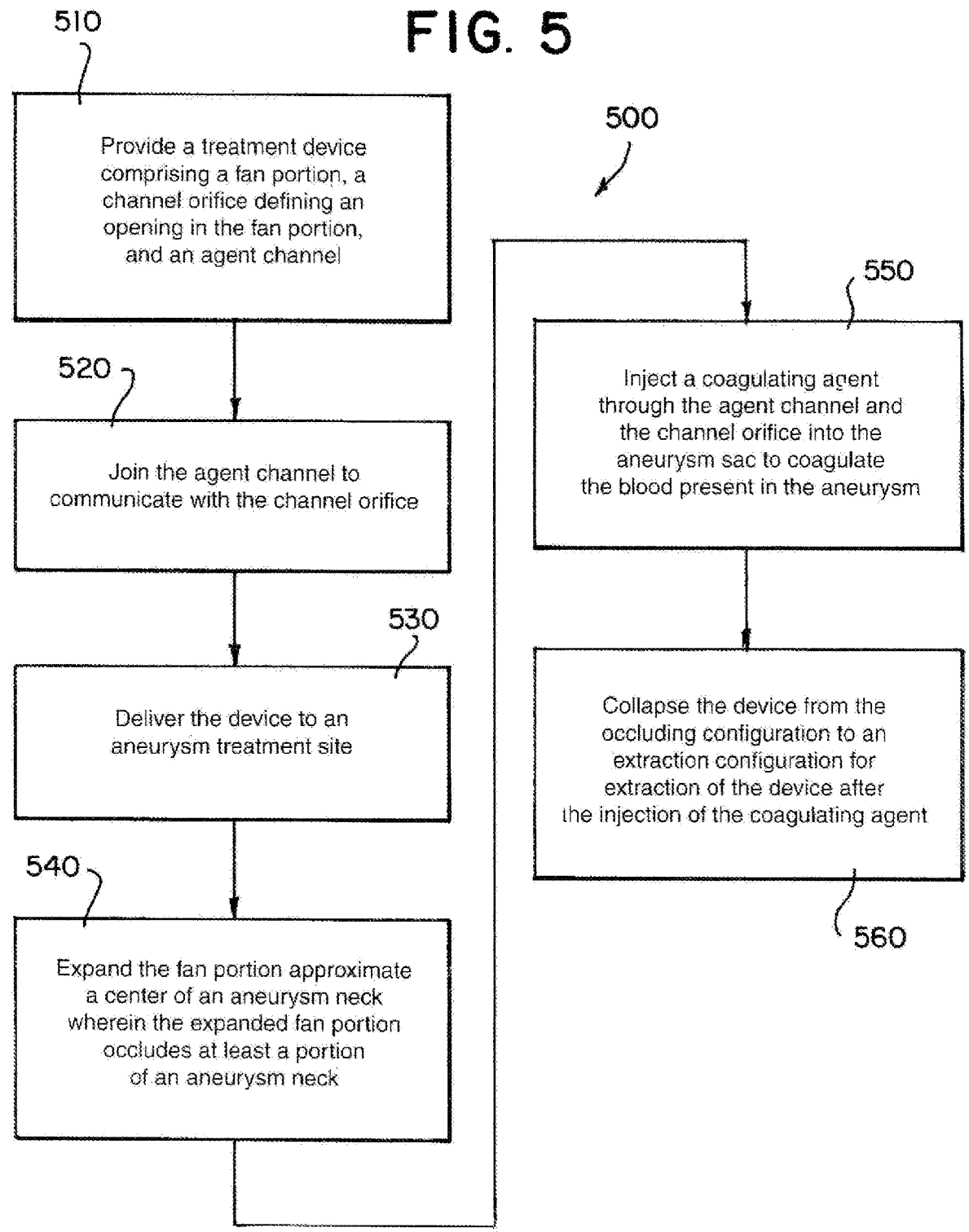

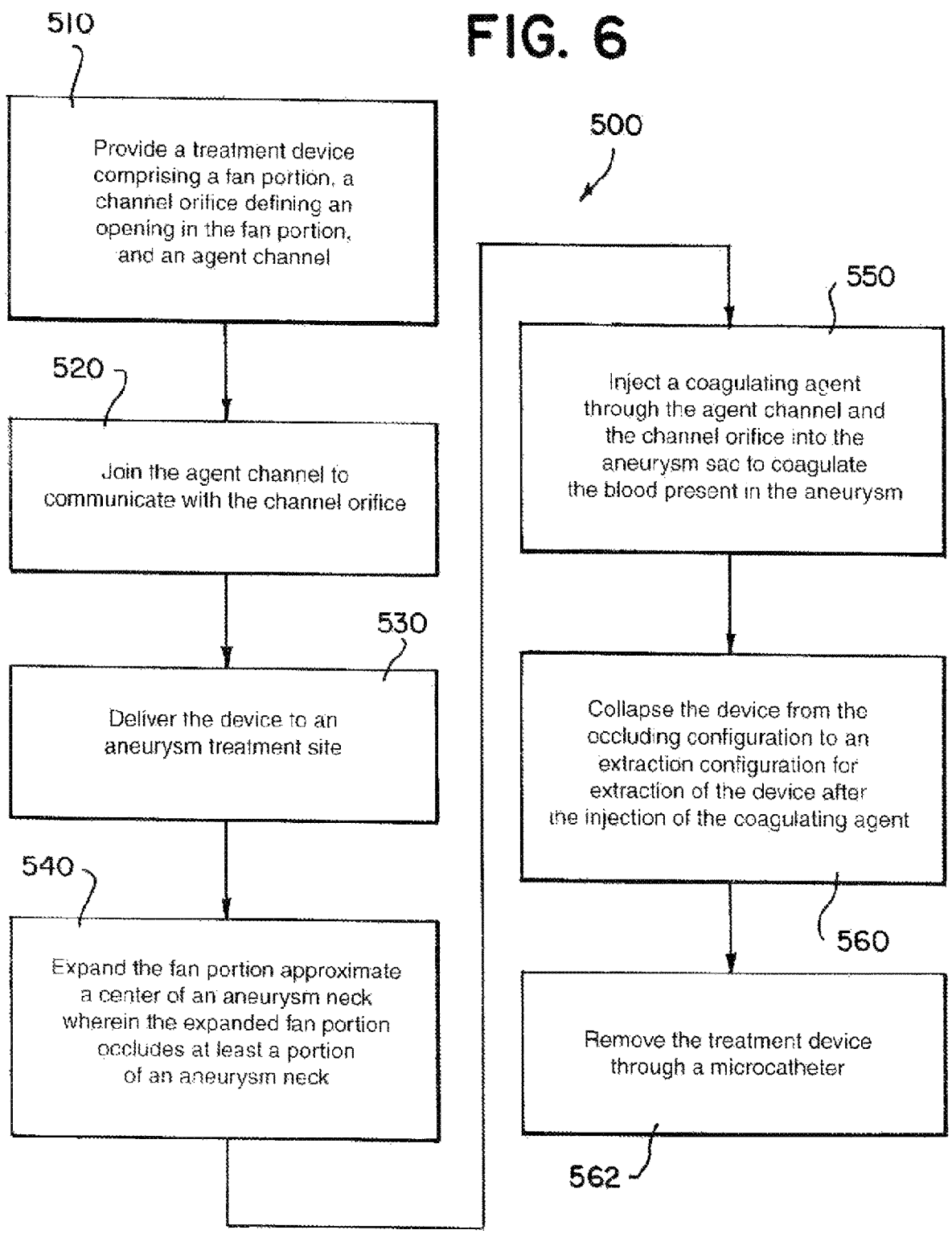

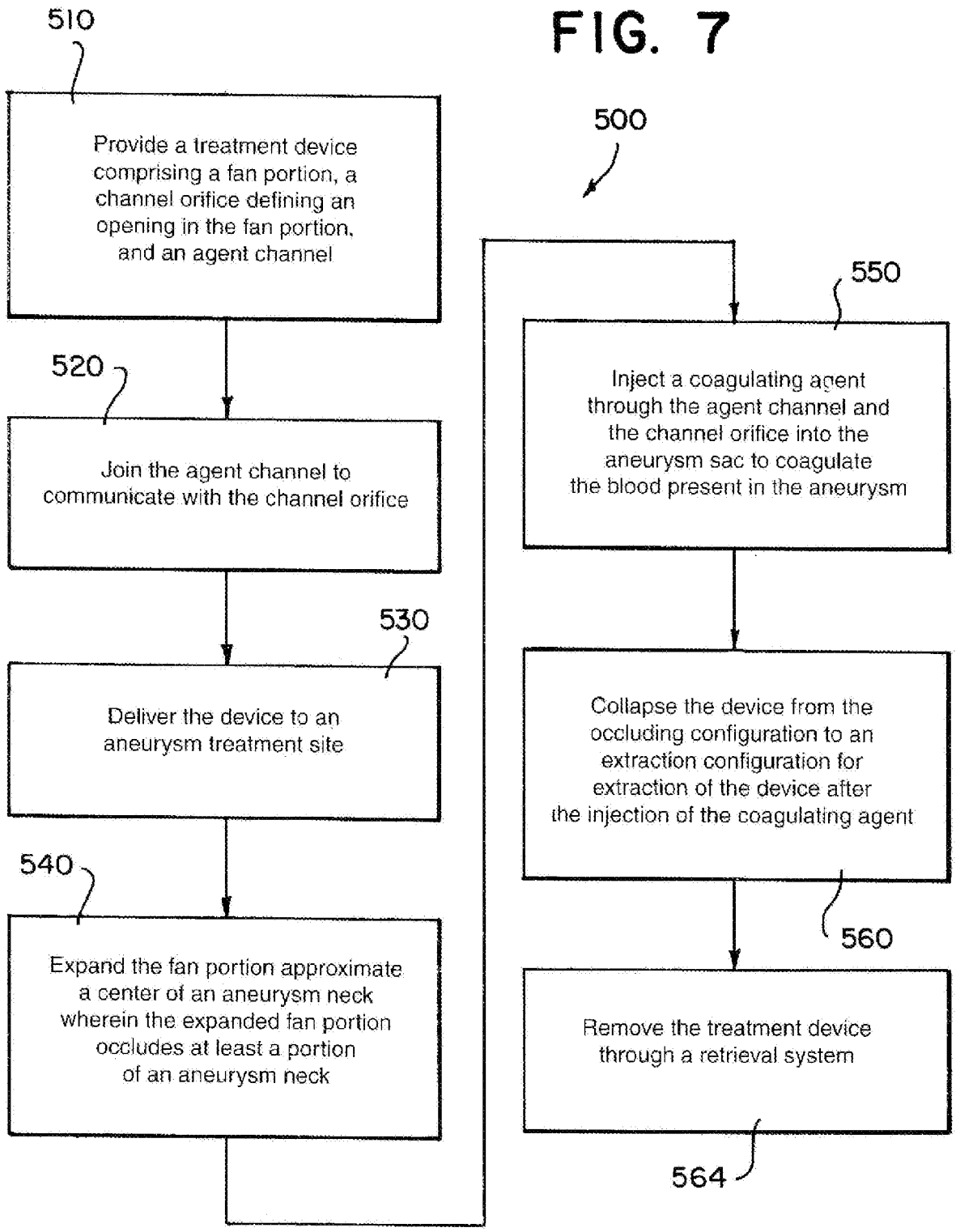

ANEURYSM OCCLUDING DEVICE FOR USE WITH COAGULATING AGENTS

FIELD OF INVENTION

The present invention generally relates to medical instruments, and more particularly, to treatment devices for aneurysm therapy.

BACKGROUND

Aneurysms can be complicated and difficult to treat. For example, treatment access can be limited or unavailable when an aneurysm is located proximate critical tissues. Such factors are of particular concern with cranial aneurysms due to the brain tissue surrounding cranial vessels and the corresponding limited treatment access.

Prior solutions have included endovascular treatment access whereby an internal volume of the aneurysm sac is removed or excluded from arterial blood pressure and flow. In this respect, because the interior walls of the aneurysm can continue being subjected to flow of blood and related pressure, aneurysm rupture remains possible.

Alternatives to endovascular or other surgical approaches can include occlusive devices. Such devices have typically incorporated multiple embolic coils that are delivered to the vasculature using microcatheter delivery systems. For example, when treating cranial aneurysms, a delivery catheter with embolic coils is typically first inserted into non-cranial vasculature through a femoral artery in the hip or groin area. Thereafter, the catheter is guided to a location of interest within the cranium. The sac of the aneurysm can then be filled with the embolic material to create a thrombotic mass that protects the arterial walls from blood flow and related pressure. However, such occlusive devices do have certain shortcomings, including mass effect, which can cause compression on the brain and its nerves. Obtaining an embolic coil packing density sufficient to either occlude the aneurysm neck or fill the aneurysm sac is difficult and time consuming. Further, aneurysm morphology (e.g. wide neck, bifurcation, etc.) can require ancillary devices such as stents or balloons to support the coil mass and obtain the desired packing density. The coils and accompanying ancillary devices can remain in patients for their entire lives. Additionally, embolic coils do not always effectively treat aneurysms as re-canalization of the aneurysm and/or coil compaction can occur over time. Many people who undergo aneurysm coil procedures also require a long period of dual antiplatelet therapy while the patient recovers post-procedure.

One particular type of occlusive approach endeavors to deliver and treat the entrance or "neck" of the aneurysm as opposed to the volume of the aneurysm by implanting a device in the parent vessel of the aneurysm. In such "neck" approaches, by minimizing blood flow across the neck, a cessation of flow into the aneurysm can be achieved. In turn, a thrombotic mass can naturally form without having to deliver embolic materials into the aneurysm sac, as previously described. However, this approach also has its drawbacks, as the aneurysm does not undergo thromboses immediately, and there is still a risk of rupture post-surgery. Therefore, there is a need for a device capable of simplified and shortened implantation procedures that can quickly inhibit blood flow in an aneurysm to increase patient safety, reduce the length of the patient recovery period, and reduce the length of antiplatelet therapy administration.

It is an aim of this invention to resolve these and other issues of the art.

SUMMARY

Disclosed herein are various exemplary devices for treating an aneurysm with a coagulating agent. The devices can generally include a fan portion for occluding an aneurysm neck, a channel orifice opening in the fan portion, and an agent channel for delivering a coagulating agent through the orifice into the aneurysm. Devices can be delivered through a catheter to the aneurysm, the fan portion can expand to occlude the aneurysm neck, and the coagulating agent can be injected into the aneurysm. During injection of the coagulating agent, the fan portion can create a barrier to inhibit the coagulating agent from exiting the aneurysm. After injection of the coagulating agent, the fan portion can collapse and the device can be extracted from the patient.

An example device for occluding an aneurysm can include a fan portion that is expandable from a collapsed configuration to an occluding configuration, a channel orifice, and an agent channel. The fan portion in the occluding configuration can occlude an aneurysm neck to create a barrier between the aneurysm and a blood vessel. This barrier can prevent the coagulating agent from leaking into the blood vessel during and/or after delivery of the agent into the aneurysm sac. The fan portion can extend across and occlude at least a portion of the aneurysm neck or can completely occlude the aneurysm neck in the occluding configuration. The channel orifice can define an opening in the fan portion through which the coagulating agent can be injected. The agent channel can be in communication with the channel orifice and can deliver the coagulating agent through the channel orifice into the aneurysm sac.

The example device can be delivered to the aneurysm using a microcatheter. The fan portion can detach from its position near the aneurysm neck after the coagulating agent has been delivered to the aneurysm sac. In another example, the fan portion can be collapsed from the occluding configuration to an extraction configuration. This extraction configuration can be sized to fit inside a retrieval catheter.

The fan portion can consist of at least one elongated support. The elongated support can be connected to an occluding element. In some examples, the elongated support can have a first end and a second end. The first end of the elongated support can be positioned near the channel orifice in the fan portion. The second end of the elongated support can extend towards a wall of the aneurysm across at least a portion of the aneurysm neck to occlude the neck when the fan portion is expanded to the occluding configuration.

The fan portion can also be inflated to reach the occluding configuration. The device can include an inflation tube to inflate the fan portion to the occluding configuration. The inflation tube can have a distal end connected to the fan portion.

The agent channel can have a proximal end and a distal end. The distal end of the agent channel can communicate with the channel orifice to transfer the coagulating agent into the aneurysm sac. The proximal end of the agent channel can receive the coagulating agent. The channel orifice can also be an opening in the distal end of the agent channel, whereby a single opening functions as both the channel orifice and the distal end of the agent channel.

The example device can further have a trigger mechanism in communication with the proximal end of the agent channel. The trigger mechanism can communicate with the proximal end of the agent channel to receive the coagulating agent or introduce the coagulating agent into the agent channel. The trigger mechanism can facilitate delivery of the coagulating agent from the proximal end to the distal end of the agent channel, and then through the channel orifice into the aneurysm sac.

In another example, a delivery apparatus for treating an aneurysm can have an agent channel that can deliver a coagulating agent to an aneurysm sac. The agent channel can have a distal end and a proximal end. The proximal end of the agent channel can receive the coagulating agent and deliver the coagulating agent from the proximal end to the distal end of the agent channel. The distal end of the agent channel can communicate with a channel orifice in a fan portion and deliver the coagulating agent through the channel orifice into the aneurysm. The channel orifice can also be an opening in the distal end of the agent channel.

In the example apparatus, the fan portion can expand from a collapsed configuration to an occluding configuration. The fan portion in the occluding configuration can extend across and occlude a portion of an aneurysm neck to create a barrier between a blood vessel and the aneurysm. This barrier can prevent the delivered coagulating agent from entering the blood vessel and help retain the coagulating agent inside the aneurysm sac.

The fan portion can detach from its position near the aneurysm neck after the coagulating agent has been delivered to the aneurysm sac. The fan portion can collapse from the occluding configuration to an extraction configuration. This extraction configuration can be sized to fit inside a retrieval catheter.

The example apparatus can further comprise a trigger mechanism in communication with the proximal end of the agent channel for receiving the coagulating agent or introducing the coagulating agent into the agent channel.

An example method for treating an aneurysm can include providing an exemplary treatment device which can include a fan portion, a channel orifice defining an opening in the fan portion, and an agent channel; joining the agent channel to the channel orifice; delivering the exemplary treatment device to an aneurysm treatment site; expanding the fan portion to an occluding configuration approximate a center of an aneurysm neck wherein the expanded fan portion occludes at least a portion of the aneurysm neck; injecting a coagulating agent through the agent channel, through the channel orifice, and into the aneurysm sac to coagulate the blood present in the aneurysm; and collapsing the treatment device from the occluding configuration to an extraction configuration for extraction of the device after the injection of the coagulating agent.

The method can include the step of creating a barrier with the fan portion between a blood vessel and the aneurysm to prevent the coagulating agent from entering the blood vessel. The method can include removing the treatment device through a microcatheter or through a retrieval deployment system. The method can include treating an aneurysm with only a single implementation step.

The method can further include providing a trigger mechanism and triggering the delivery of the agent by activating the trigger mechanism at a proximal end of the agent channel to deliver the agent from the proximal end of the agent channel to a distal end of the agent channel.

BRIEF DESCRIPTION OF THE DRAWINGS

The above and further aspects of this invention are further discussed with reference to the following description in conjunction with the accompanying drawings, in which like numerals indicate like structural elements and features in various figures. The drawings are not necessarily to scale, emphasis instead being placed upon illustrating principles of the invention. The figures depict one or more implementations of the inventive devices, by way of example only, not by way of limitation.

FIGS. 2a to 2f are illustrations of a treatment sequence of an exemplary treatment device and delivery of a coagulating agent to an aneurysm according to aspects of the present invention;

FIGS. 3a to 3e are illustrations of a treatment sequence of an exemplary inflatable treatment device and delivery of a coagulating agent to an aneurysm according to aspects of the present invention;

FIG. 5 is a flow diagram outlining example method steps that can be carried out during delivery and use of a treatment device according to aspects of the present invention.

FIG. 6 is a flow diagram outlining example method steps that can be carried out during delivery and use of a treatment device according to aspects of the present invention.

FIG. 7 is a flow diagram outlining example method steps that can be carried out during delivery and use of a treatment device according to aspects of the present invention.

DETAILED DESCRIPTION

The descriptions contained herein are examples of the invention and are not intended in any way to limit the scope of the invention. In general, example devices described herein describe a treatment device that can be placed over the neck of an aneurysm to create a barrier between a vessel and the aneurysm. At least one coagulating agent can then delivered into the aneurysm sac. Delivery can be activated via trigger mechanism on the proximal end of the delivery system. The device can be held approximate the aneurysm neck at least until the coagulating agent is injected, and then can be retracted or detached from the aneurysm. The rapid coagulating agents can coagulate the blood in the aneurysm instantly. In some examples, the device can be removed via a microcatheter or deployed via a retrieval deployment system.

The example devices can include a fan portion that can expand from a collapsed configuration to an occluding configuration in which the fan portion in the occluding configuration is shaped to occlude an aneurysm neck from within an aneurysm sac. In the occluding configuration, the fan portion can generally have a channel orifice working in connection with an agent channel that delivers a coagulating agent through the channel orifice and into the aneurysm sac.

It must be noted that, as used in the specification and the appended claims, the singular forms "a," "an" and "the" include plural referents unless the context clearly dictates otherwise. By "comprising" or "containing" or "including" it is meant that at least the named compound, element, particle, or method step is present in the composition or article or method, but does not exclude the presence of other compounds, materials, particles, method steps, even if the other such compounds, material, particles, method steps have the same function as what is named.

In describing examples, terminology will be resorted to for the sake of clarity. It is intended that each term contemplates its broadest meaning as understood by those skilled in the art and includes all technical equivalents that operate in a similar manner to accomplish a similar purpose. It is also to be understood that the mention of one or more steps of a method does not preclude the presence of additional method steps or intervening method steps between those steps expressly identified. Steps of a method can be performed in a different order than those described herein without departing from the scope of the disclosed technology. Similarly, it is also to be understood that the mention of one or more components in a device or system does not preclude the presence of additional components or intervening components between those components expressly identified.

Figure 1:
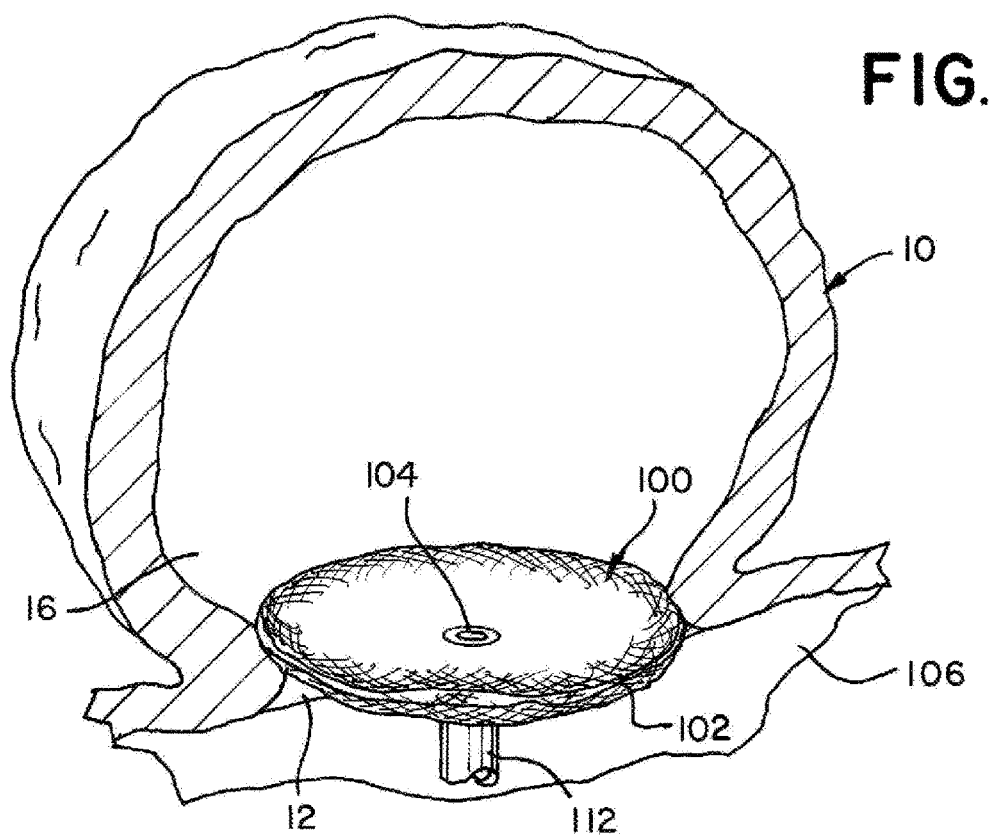
FIG. 1 is an illustration of an exemplary treatment device positioned to occlude an aneurysm neck according to aspects of the present invention.

Turning to FIG. 1, an example treatment device 100 is shown with the fan portion 102 in an occluding configuration approximate the neck 12 of an aneurysm 10. The fan portion 102 can occlude the aneurysm 10 from inside the aneurysm sac 16. The fan portion 102 in the occluding configuration can be sized to occlude at least a portion of the aneurysm neck 12. The fan portion 102 in the occluding configuration can completely occlude the aneurysm neck 12 as depicted in FIG. 1. The fan portion 102 in the occluding configuration can occlude the neck 12 to create a barrier between a blood vessel 106 and the aneurysm 10. The fan portion 102 can contain a channel orifice 104. As illustrated, the channel orifice 104 can be located in the fan portion 102 such that the channel orifice 104 opens up to the aneurysm 10. The channel orifice 104 can be centrally located in the fan portion 102. The channel orifice can work in connection with an agent channel 112.

FIGS. 2a through 2f are illustrations of stages or steps that can occur during a treatment sequence of an exemplary treatment device 100 and delivery of a coagulating agent 114 to an aneurysm 10. The coagulating agent 114 can be a drug based on replacement factors, vitamin K, antiplasmins or any other drugs known to those of skill in the art that can affect blood clotting. In some examples, a rapidly clotting drug can be effective. In addition, the drug needs to be deliverable through a torturous agent channel 112.

Figure 2A:
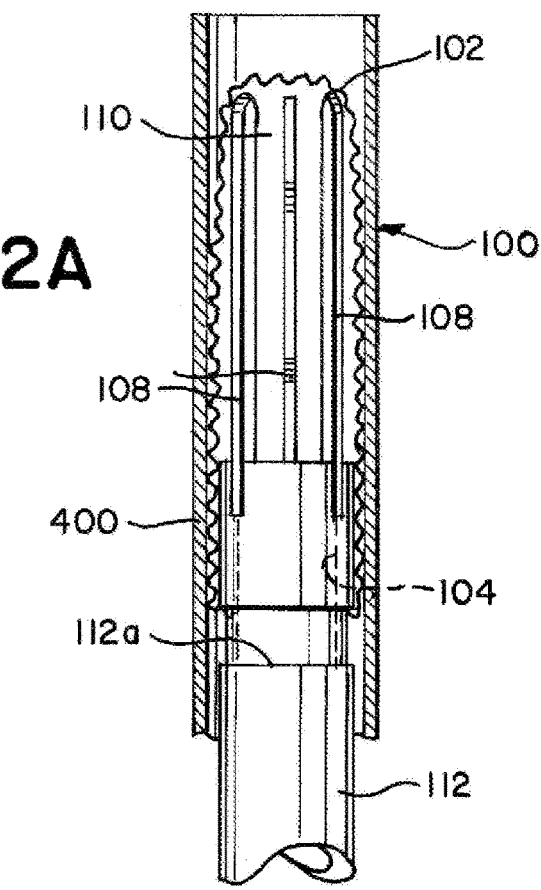

FIG. 2a is an illustration of an example treatment device 100 wherein the fan portion 102 is shown in a collapsed delivery configuration inside a delivery catheter 400, a channel orifice 104 positioned on a proximal end of the collapsed fan portion 102, and an agent channel 112 attached to the channel orifice 104. The fan portion 102 can be sized to fit within the lumen of a delivery catheter 400 when the fan portion 102 is in the collapsed configuration. The treatment device 100 in its entirety can be sized to fit within the lumen of a delivery catheter 400 when the fan portion 102 is in the collapsed configuration. When the fan portion 102 is in the collapsed configuration, the fan portion 102 can have sufficient flexibility to be delivered through the delivery catheter 400, navigating torturous anatomical geometries, to be delivered to an aneurysm 10 (not shown). The agent channel 112 can have sufficient length to be accessible outside of the patient when the fan portion 102 reaches a treatment site. The fan portion 102 in the collapsed configuration can have a substantially tubular shape. The fan portion 102 can be comprised of at least one elongated support 108. The example in FIG. 2a shows three elongated supports 108 comprising the fan portion 102. An occluding element 110 can be attached to the one or more elongated supports 108.

Figure 2B:
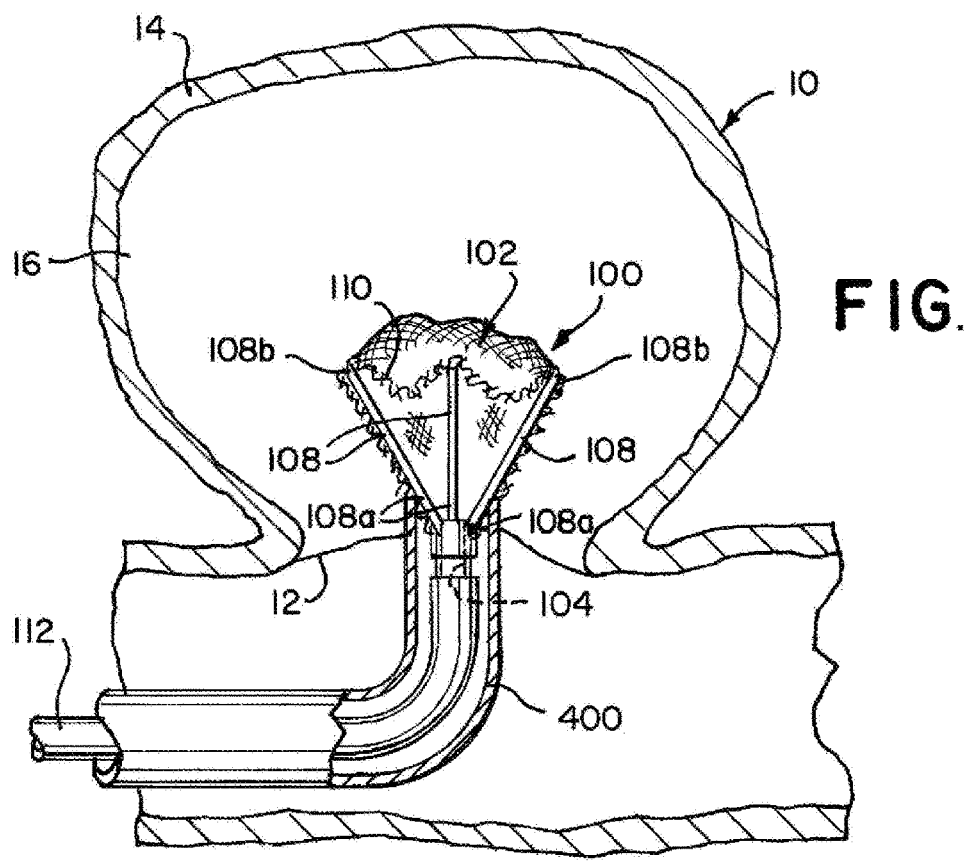

Moving on to FIG. 2b, the treatment device 100 can be delivered to an aneurysm 10 by sliding the device 100 distally when the fan portion 102 is in a collapsed configuration through a delivery catheter 400. The treatment device 100 can be delivered to a treatment site through a blood vessel 106. FIG. 2b illustrates the treatment device 100 inside the delivery catheter 400 located near an aneurysm neck 12. FIG. 2b further shows the fan portion 102 pushed partially out of the delivery catheter 400 for deployment inside the aneurysm sac 16. The fan portion 102 can expand as it exits the delivery catheter 400. The fan portion 102 can include a memory shape material such as Nitinol, a Nitinol alloy, a polymer memory shape material, or other memory shape material having properties for reshaping as described herein. The fan portion 102 can be in a deformed shape in the collapsed configuration and reshape based on a predetermined shape after exiting the delivery catheter 400. As illustrated in FIG. 2b, each elongated support 108 of the fan portion 102 can have a first end 108a positioned approximate the channel orifice 104, and a second end 108b extending from the first end 108a across at least a portion of the aneurysm neck 12 towards an aneurysm wall 14. The second end 108b can extend towards the interior wall 14 of the aneurysm 10 upon expansion of the fan portion 102. When each elongated support 108 expands, the elongated support 108 can in turn expand the connected occluding element 110 to occlude at least a portion of the aneurysm neck 12. In another example, the occluding element 110 can expand upon discharge from the delivery catheter 400 and cause the second end 108b of each connected elongated support 108 to move towards the aneurysm wall 14.

Figure 2C:
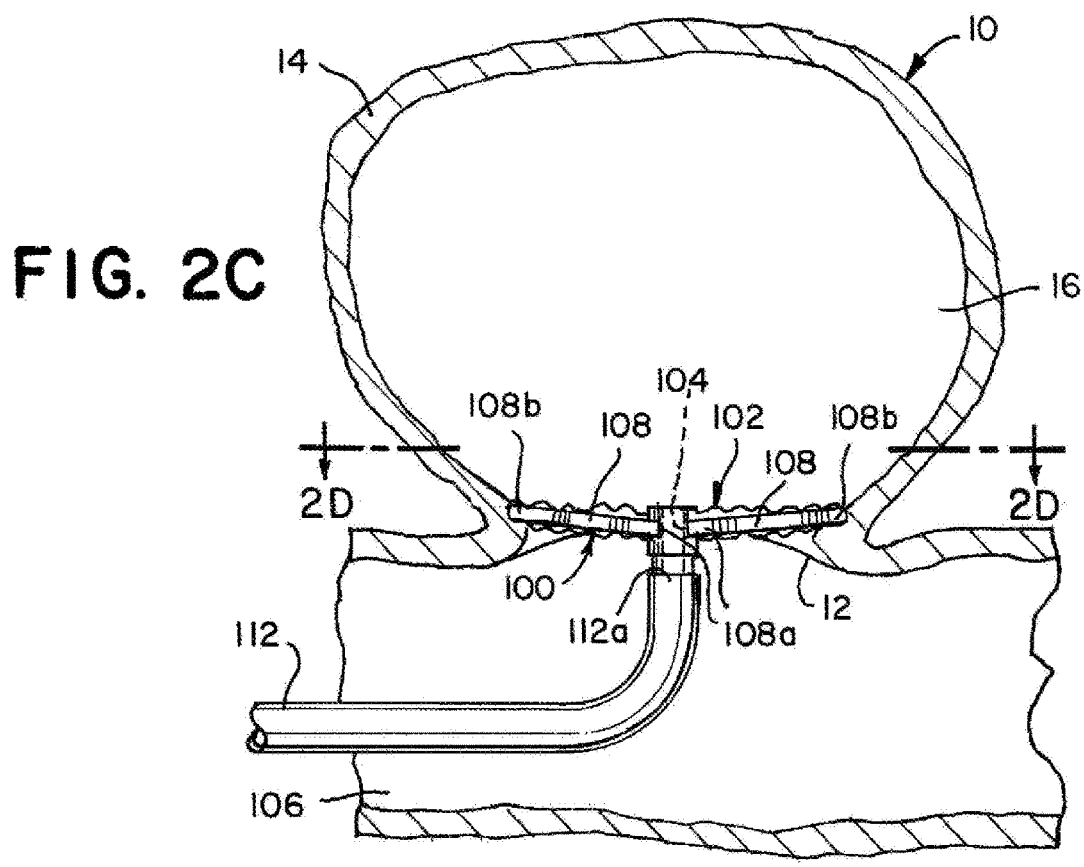

FIG. 2c illustrates the example treatment device 100 wherein the fan portion 102 is in an occluding configuration in the aneurysm 10. The fan portion 102 in the occluding configuration can be sized to occlude at least a portion of an aneurysm neck 12. The fan portion 102 in the occluding configuration can completely occlude the aneurysm neck 12 as depicted in FIG. 2c. The fan portion 102 in the occluding configuration can occlude the neck 12 to create a barrier between a blood vessel 106 and the aneurysm 10. As illustrated in FIG. 2c, the second end 108b of the elongated support 108 can be in contact with the aneurysm wall 14 when the fan portion 102 is in the occluding configuration. In occluding configuration, the fan portion 102 can be capable of deflecting a blood flow from the aneurysm 10, diverting a blood flow from the aneurysm 10, slowing a blood flow into the aneurysm 10, or any combination thereof.

In the occluding configuration, the fan portion 102 can extend to the aneurysm wall 14, and the fan portion 102 can provide a force against the aneurysm wall 14 to maintain the expanded position of the fan portion 102 such that the treatment device 100 doesn't become dislodged and become ineffective at inhibiting blood flow into the aneurysm. The force of the fan portion 102 to the aneurysm wall 14 can be sufficient to maintain the position of the treatment device 100 within the aneurysm 10. For example, the fan portion 102 can be made of a memory shape material having a first, predetermined shape and a second, collapsed shape in the collapsed configuration. When the fan portion 102 is in an occluding configuration within the aneurysm 10, the fan portion 102 can move to a third, deployed shape that is based at least in part on the first, predetermined shape and the anatomical geometry of the aneurysm 10. In the example, the first, predetermined shape can be sized larger than the wall 14 within the aneurysm sac 16; the fan portion 102 can move to extend to the wall 14; and the fan portion 102 can provide a force against the wall 14 as the properties of the memory shape material cause the fan portion 102 to attempt to open to the predetermined shape. The fan portion 102 in the occluding configuration can take the shape of the aneurysm neck 12 and/or interior walls 14 of the aneurysm near the aneurysm neck 12.

Figure 2D:
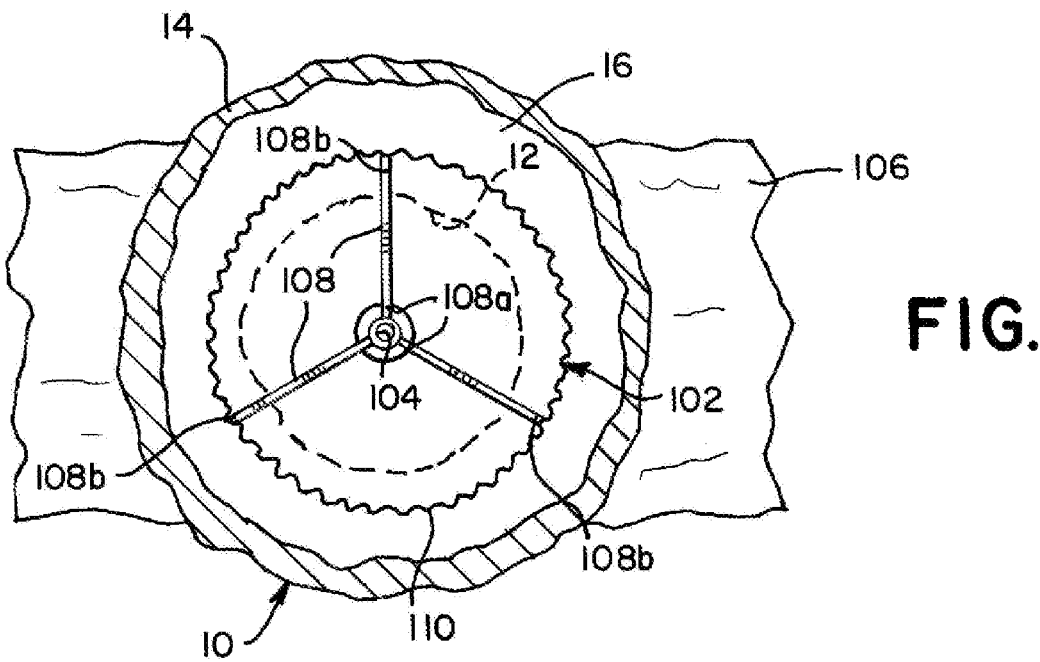

FIG. 2*d* is an illustration of a cross-sectional view looking distally into the aneurysm 10 of an example treatment device 100 where the fan portion 102 is in the occluding configuration, such as the treatment device 100 depicted in FIG. 2*c*.

Figure 2E:
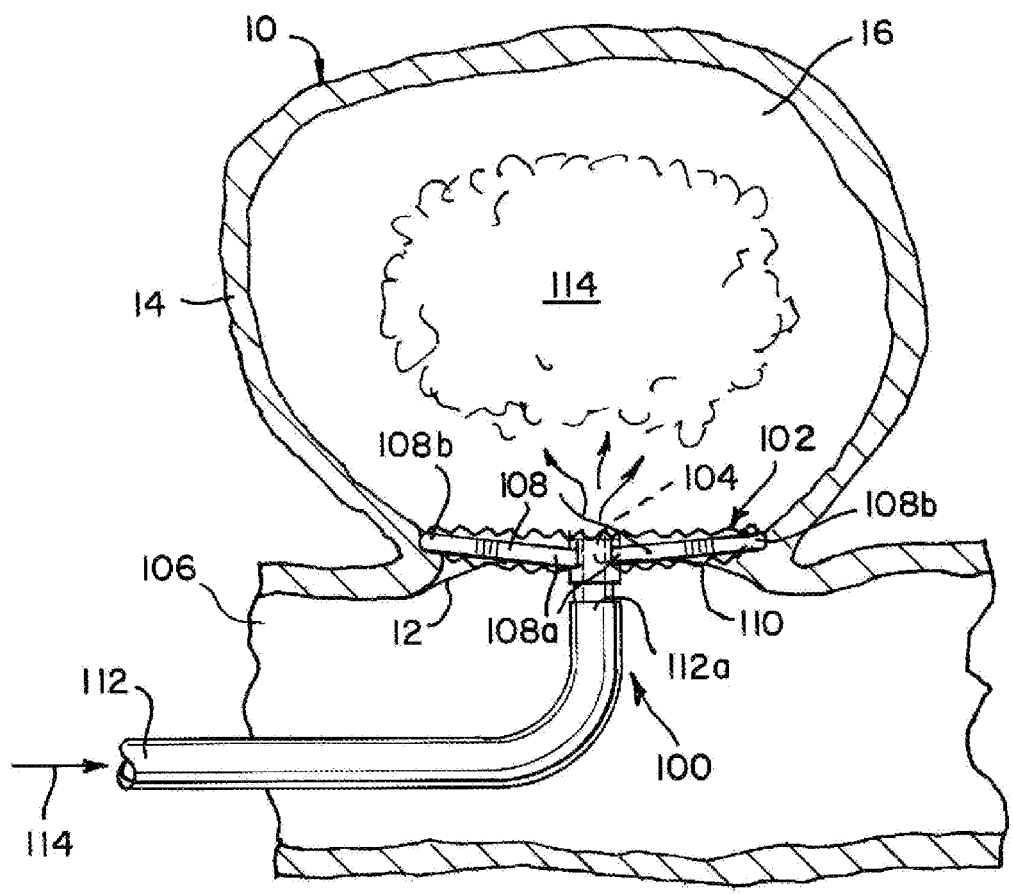

FIG. 2*e* illustrates the treatment device 100 wherein the fan portion 102 is in the occluding configuration. The channel orifice 104 in the fan portion 102 can work in connection with an agent channel 112. The agent channel 112 can allow for the transfer of one or more coagulating agents 114 through the channel 112 to the channel orifice 104. The coagulating agent 114 can include rapid coagulating agents, such as collagen, chitosan, kaolin, zeolite, or other agents having properties for coagulating as described herein. The agent channel 112 can have a distal end 112*a* a proximal end (not shown). The distal end 112*a* of the agent channel 112 can connect to the channel orifice 104. The proximal end can receive the coagulating agent 114 into the agent channel 112 and deliver the coagulating agent 114 from the proximal end to the distal end 112*a* connected to the channel orifice 104. The proximal end can be accessible outside of the patient for injection of the coagulating agent 114 into the patient. Coagulating agent 114 passing through the lumen of the agent channel 112 to the distal end 112*a* can subsequently pass through the channel orifice 104 and into the aneurysm sac 16 upon reaching the distal end 112*a* of the agent channel 112. The distal end 112*a* of the agent channel 112 can also be the channel orifice 104 of the fan portion 102. The coagulating agent 114 can coagulate the blood inside the aneurysm 10. The coagulating agent 114 can coagulate the blood inside the aneurysm 10 virtually instantaneously upon contacting the blood inside the aneurysm 10 according to the coagulation properties of the coagulating agent 114.

As shown in FIG. 2*f*, once the coagulating agent 114 has been pumped into the aneurysm sac 16, the treatment device 100 can be removed from the aneurysm 10. The treatment device 100 can be removed once the coagulating agent 114 has coagulated the blood in the aneurysm 10. The treatment device 100 can detach from its location approximate the aneurysm neck 12 after delivery of the coagulating agent 114. As in the device shown in FIG. 2*e*, the occluding element 110, the elongated supports 108, or both the occluding element 110 and the elongated supports 108 can detach from their location approximate the aneurysm neck 12 after delivery of the coagulating agent 114. In another example, the treatment device 100 can be removed via a retrieval deployment system. In another example, the fan portion 102 (not shown) can collapse from the occluding configuration to an extraction configuration after the coagulating agent 114 has been delivered to the aneurysm sac 16. The extraction configuration can be sized to traverse through a lumen of a catheter (not shown). The aneurysm 10, now filled with the coagulating agent 114 can now start to be reabsorbed into the blood vessel 106 through the body's natural healing process. This can avoid the need for permanently implanted elements in the patient.

Figure 3C:
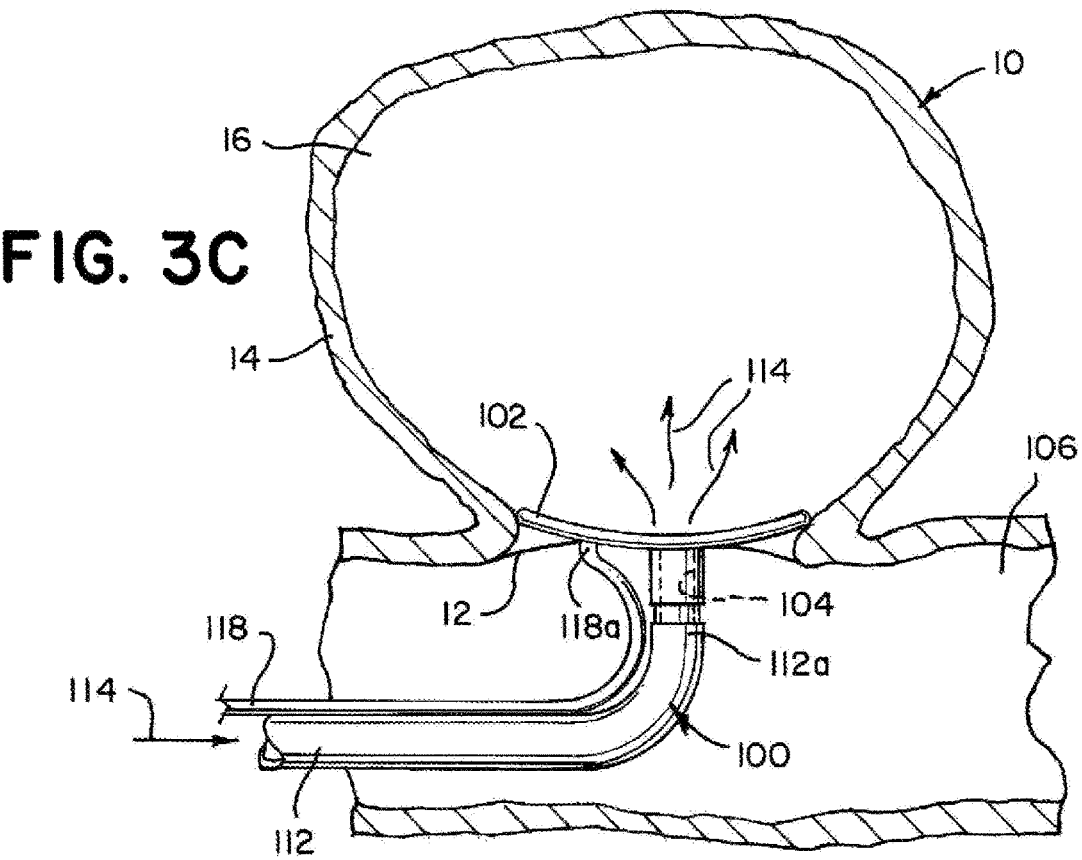

FIGS. 3*a* to 3*e* are illustrations of stages or steps that can occur during another example implementation sequence of an exemplary treatment device 100. FIG. 3*a* illustrates an example treatment device 100 comprising a fan portion 102 having a channel orifice 104, an agent channel 112 connected to the channel orifice 104 at a distal end 112*a* of the agent channel 112, and an inflation tube 118 connected to the fan portion 102. The fan portion 102 is shown in a collapsed delivery configuration inside a delivery catheter 400. The fan portion 102 can be in connection with the inflation tube 118 which can inflate the fan portion 102. The fan portion 102 can include at least one material used in neurovascular balloons, such as polyurethane or silicon. The inflation tube 118 can have a distal end 118*a* connected to the fan portion 102.

FIG. 3*b* illustrates the treatment device 100 inside the delivery catheter 400 with the fan portion 102 exiting the delivery catheter 104 for deployment inside a sac 16 of an aneurysm 10. As shown in FIG. 3*b*, the fan portion 102 can be inflated to expand using the inflation tube 118 as it exits the delivery catheter 400. The fan portion 102 can be completely removed from the delivery catheter 400 before inflation begins. Alternatively, inflation of the fan portion 102 can begin while the fan portion 102 is still entirely or partially inside the delivery catheter 400. Inflation of the fan portion 102 can occur using saline or a variety of other elements known in the art with respect to inflating neurovascular balloons. As the fan portion 102 inflates, the outer surface of the fan portion 102 can expand towards the aneurysm wall 14.

FIG. 3*c* illustrates the treatment device 100 wherein the fan portion 102 is in an occluding configuration in the aneurysm 10. As illustrated in FIG. 3*c*, fan portion 102 can inflate to the extent that the fan portion 102 can be in contact with the aneurysm wall 14 when the fan portion 102 is in the occluding configuration. FIG. 3*c* illustrates the delivery of a coagulating agent 114 to the aneurysm sac 16 in the same manner as described in FIG. 2*e*.

Figure 3D:
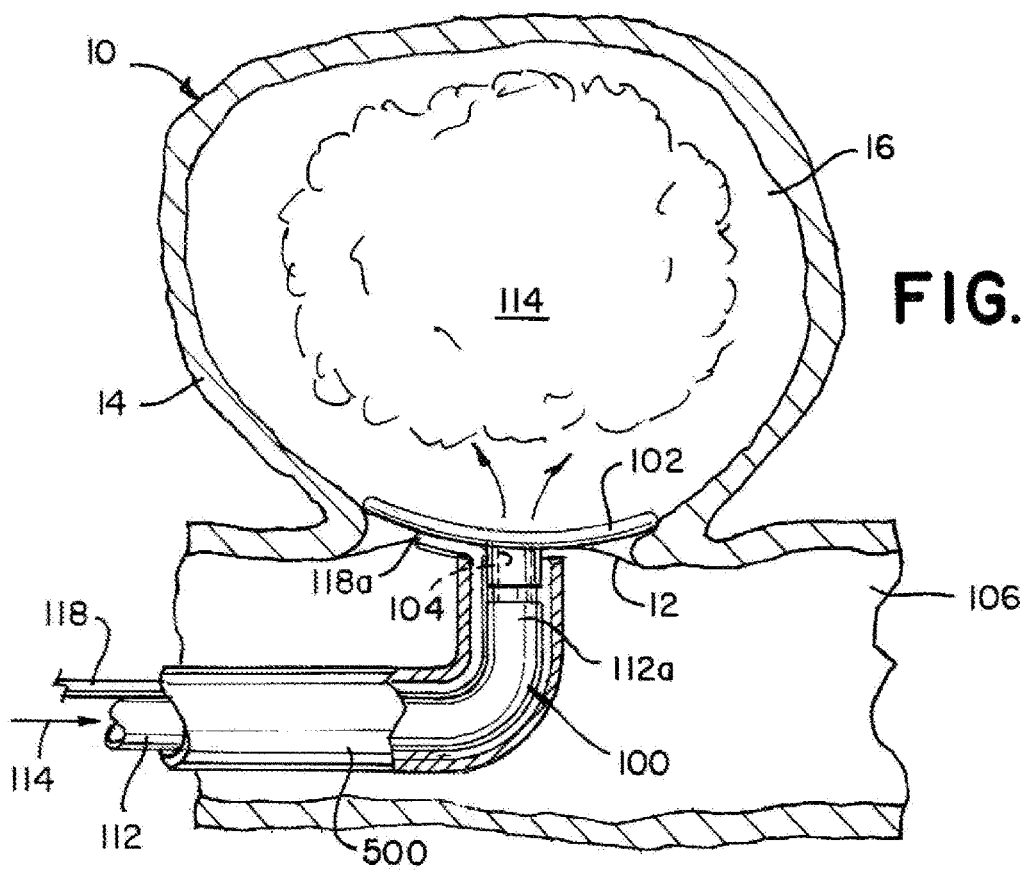
Figure 3E:
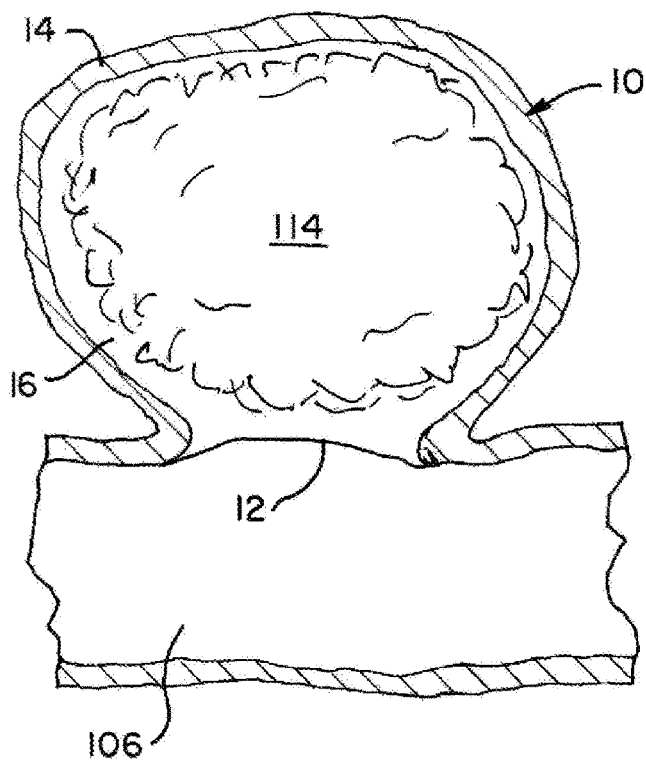

FIG. 3*d* illustrates coagulation agent 114 delivered into the aneurysm sac 16 and a retrieval catheter 500 in place to extract the device 100. The fan portion 102 can collapse from the occluding configuration to an extraction configuration after the coagulating agent 114 has been delivered to the aneurysm sac 16. The extraction configuration can be sized to traverse through a lumen of the retrieval catheter 500. The treatment device 100 can be extracted using the retrieval catheter 500 or a deployment and retrieval device. The delivery catheter 400 can also be the retrieval catheter 500. FIG. 3*e* illustrates the aneurysm following extraction of the retrieval catheter 500 and the treatment device 100. Once the coagulating agent 114 has been pumped into the aneurysm sac 16, the fan portion 102 can detach from its location approximate the aneurysm neck 12. The fan portion 102 can deflate from the occluding configuration to an extraction configuration after the coagulating agent 114 has been delivered to the aneurysm sac 16.

Figure 4A:
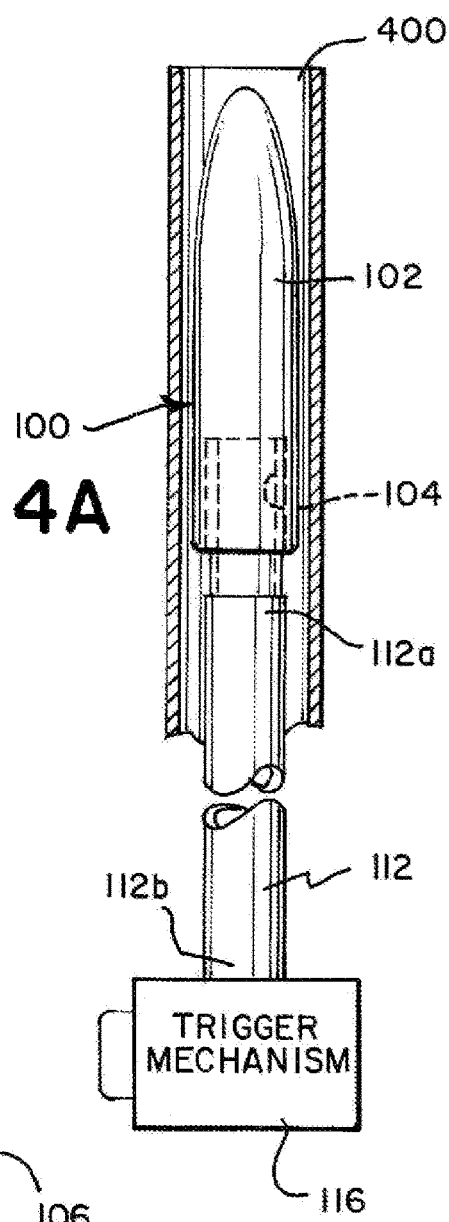
FIGS. 4a to 4e are illustrations of a treatment sequence of an exemplary treatment device in connection with a trigger mechanism and delivery of a coagulating agent to an aneurysm according to aspects of the present invention.

FIGS. 4*a* to 4*e* are illustrations of stages or steps that can occur during another example implementation sequence of an exemplary treatment device 100. FIG. 4*a* is an illustration of an example treatment device 100 including a fan portion 102, a channel orifice 104, an agent channel 112, and a trigger mechanism 116. The fan portion 102 is shown in a collapsed delivery configuration inside a delivery catheter 400. The fan portion 102 can contain the channel orifice 104 that can be in communication with an agent channel 112. The agent channel 112 can have a proximal end 112*b* in communication with the trigger mechanism 116. The proximal end 112*b* of the agent channel 112 can receive the coagulating agent 114 into the agent channel 112 for delivery. The trigger mechanism 116 can facilitate the delivery of the coagulating agent to an aneurysm sac 16 (not shown).

Figure 4B:
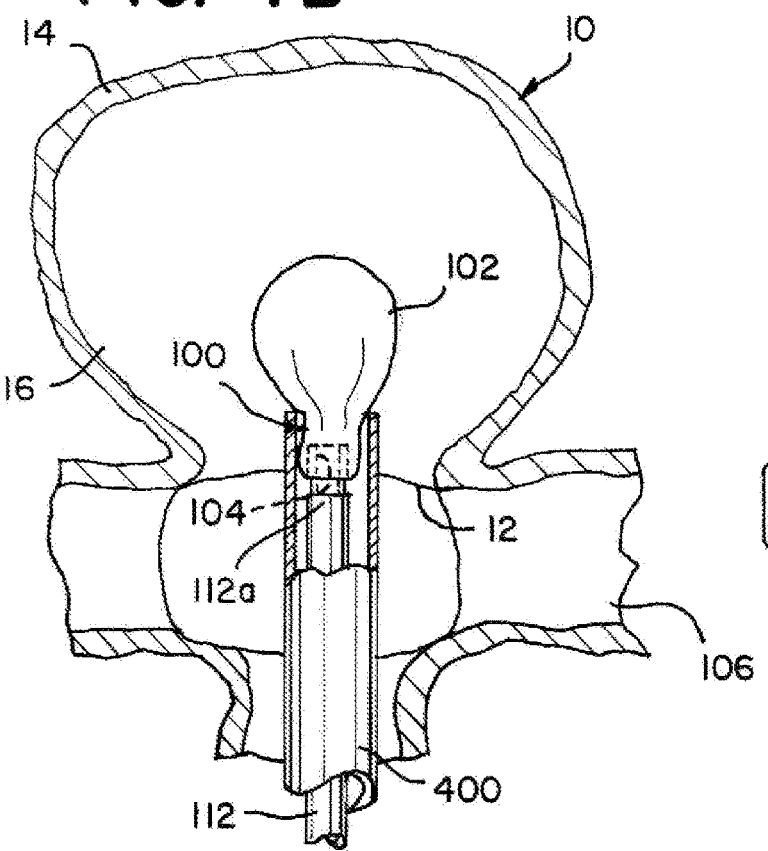
Figure 4C:
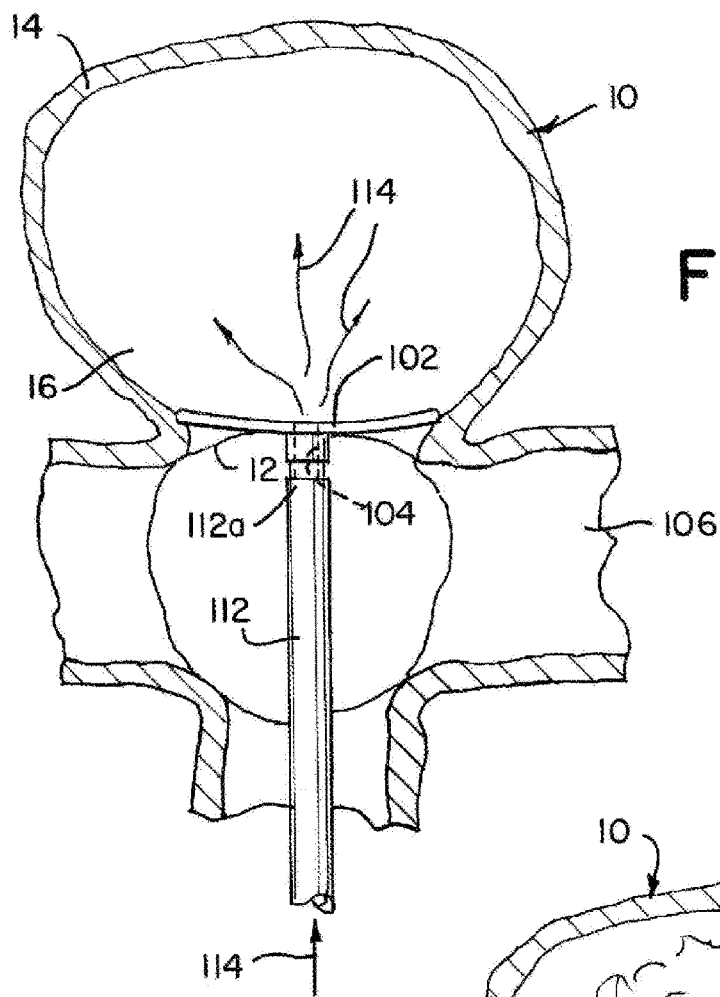
Figure 4D:
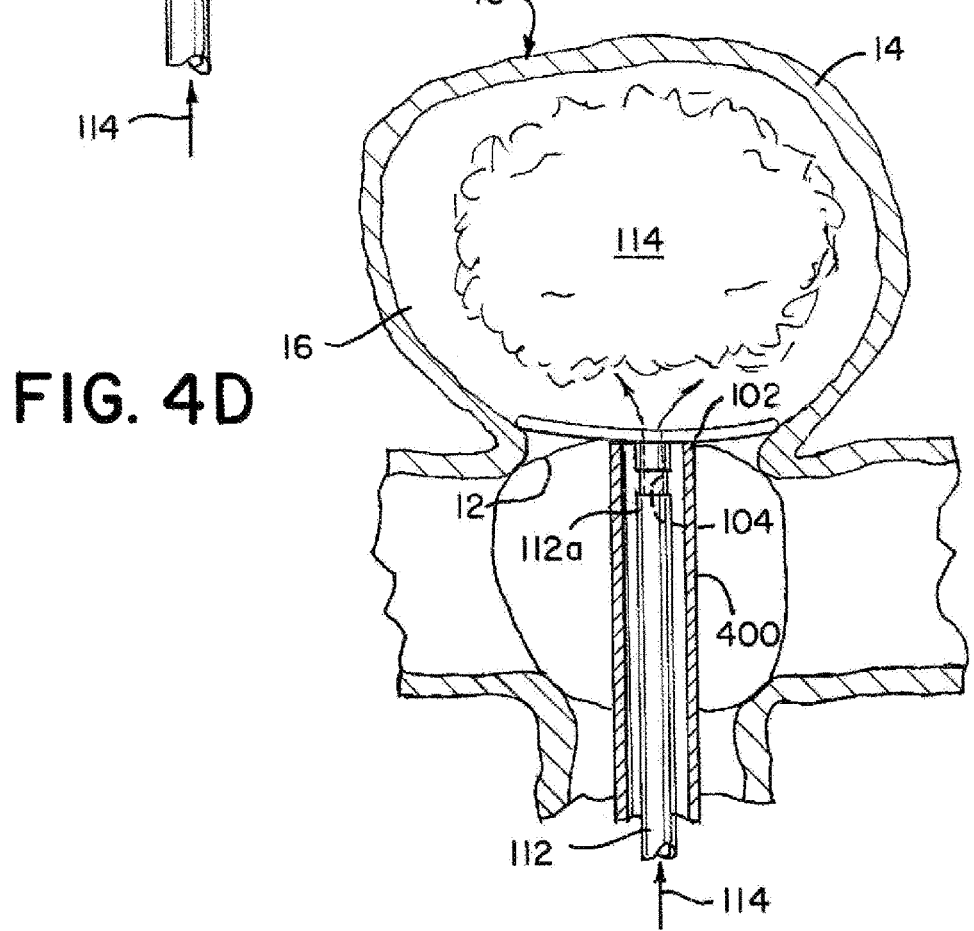

FIG. 4b illustrates the treatment device 100 inside the delivery catheter 400 with the fan portion 102 exiting the delivery catheter 400 for deployment inside the aneurysm sac 16. As illustrated in FIGS. 4b to 4d, the treatment site can include an aneurysm 10 positioned adjacent bifurcated blood vessel branches and the treatment device 100 can be delivered to the aneurysm 10 through a stem branch 106 feeding the bifurcated blood vessel branches.

Figure 4E:
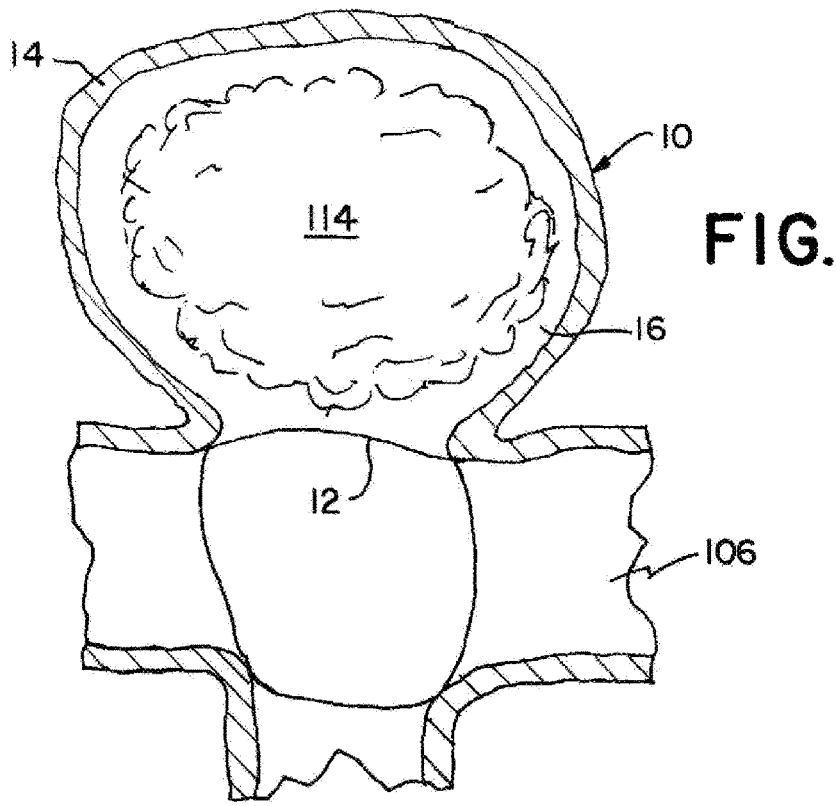

FIG. 4c illustrates the treatment device 100 wherein the fan portion 102 is in an occluding configuration in the aneurysm 10. Upon the fan portion reaching the occluding configuration, the trigger mechanism 116 can facilitate the delivery of the coagulating agent 114 through the agent channel 112 to the aneurysm sac 16. The trigger mechanism 116 can be operated to release the coagulating agent 114 by a physician, nurse, or other medical professional. FIG. 4d illustrates the delivery of a coagulating agent 114 to the aneurysm sac 16 in the same manner as described in FIG. 2e. FIG. 4e illustrates the aneurysm following extraction of the retrieval catheter 500 and the treatment device 100.

FIG. 5 is a flow diagram outlining example method steps that can be carried out during the administration of a treatment device 100. The method steps can be implemented by any of the example means described herein or by any means that would be known to one of ordinary skill in the art.

Referring to a method 500 outlined in FIG. 5, in step 510 the treatment device having a fan portion, a channel orifice defining an opening in the fan portion, and an agent channel can be provided for administration to a patient. In step 520, the agent channel can be joined to communicate with the channel orifice. In step 530, the treatment device can be delivered to an aneurysm treatment site. In step 540, the fan portion can be expanded to the occluding configuration approximate a center of an aneurysm neck. When the fan portion is expanded to the occluding configuration in step 540, the fan portion can occlude at least a portion of an aneurysm neck. Step 540 can also create a barrier between a blood vessel and the aneurysm to prevent the coagulating agent from entering the blood vessel. In step 550, the coagulating agent can be injected through the agent channel and the channel orifice into the aneurysm sac to coagulate the blood present in the aneurysm. In step 560, the treatment device can be collapsed from the occluding configuration to the extraction configuration for extraction of the device after the injection of the coagulating agent. Method 500 can further comprise the step of treating an aneurysm with only a single implementation step.

Figure 8:
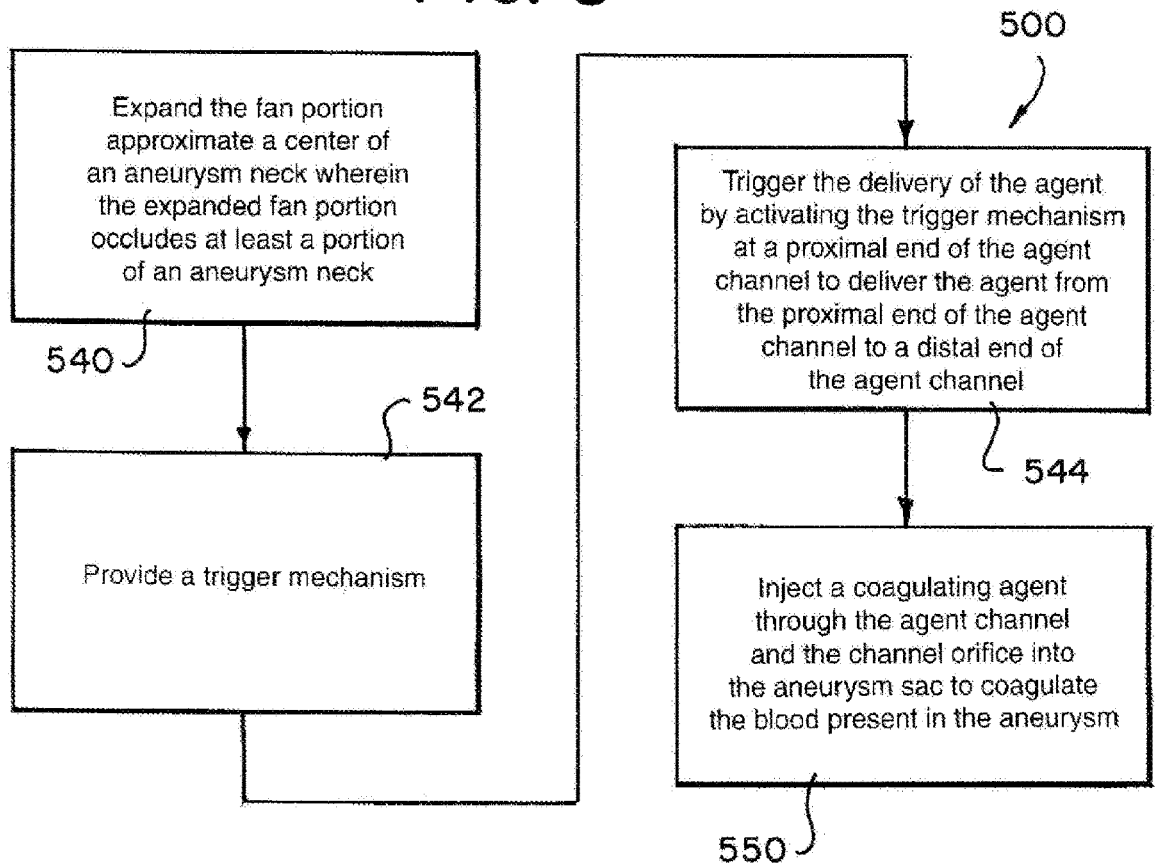
FIG. 8 is a flow diagram outlining example method steps that can be carried out during delivery and use of a treatment device according to aspects of the present invention.

FIG. 6 is a flow diagram outlining further steps of method 500. Method 500 can further comprise step 562 of removing the treatment device through a microcatheter. FIG. 7 is a flow diagram outlining further steps of method 500. Method 500 can further comprise step 564 of removing the treatment device through a retrieval system. FIG. 8 is a flow diagram outlining further steps of method 500. Method 500 can further comprise the steps of providing a trigger mechanism (step 542) and triggering the delivery of the agent by activating the trigger mechanism at a proximal end of the agent channel to deliver the agent from the proximal end of the agent channel to a distal end of the agent channel (step 544).

It should be apparent to those skilled in the art that the present teachings apply equally to the delivery apparatus 100 and treatment device 100 claimed herein. The descriptions contained herein are examples of the invention and are not intended in any way to limit the scope of the invention. As described herein, the invention contemplates many variations and modifications of the device for occluding an aneurysm, including alternative geometries of elements and components described herein, utilizing any number of known means for braiding, knitting, weaving, or otherwise forming the fan portion as is known in the art, utilizing any of numerous materials for each component or element (e.g. radiopaque materials, memory shape materials, etc.), utilizing additional components including components to deliver a treatment device to an aneurysm or eject an treatment device from a delivery catheter, or utilizing additional components to perform functions not described herein, such as coagulating agents and deployment devices, for example. These modifications would be apparent to those having ordinary skill in the art to which this invention relates and are intended to be within the scope of the claims which follow.

The invention claimed is:

1. A treatment device for treating an aneurysm, the treatment device comprising:
    a fan portion expandable from a collapsed configuration to an occluding configuration, the occluding configuration sized to extend across and occlude at least a portion of a neck of the aneurysm, the fan portion comprising at least one elongated support and an occluding element affixed to each elongated support;
    a channel orifice defining an opening in the fan portion, wherein in the occluding configuration the channel orifice is open to the aneurysm; and
    an agent channel joined to the channel orifice in the collapsed configuration for delivering a coagulating agent to an aneurysm sac through the channel orifice,
    wherein each elongated support comprises a first end positioned approximate the channel orifice and a second end positioned in a distal direction in relation to the channel orifice when the fan portion is in the collapsed configuration, the second end being configured to extend towards an interior aneurysm wall and to be in contact with the interior wall of the aneurysm proximate to the neck of the aneurysm when the fan portion expands to the occluding configuration.

2. The treatment device of claim 1 wherein the occluding configuration is configured to occlude the neck to create a barrier between a blood vessel and the aneurysm to prevent the coagulating agent from entering the blood vessel.

3. The treatment device of claim 1 wherein the fan portion is further collapsible from the occluding configuration to an extraction configuration following delivery of the coagulating agent to the aneurysm sac, the extraction configuration sized to traverse through a lumen of a retrieval catheter.

4. The treatment device of claim 1 wherein the fan portion is detachable from the aneurysm neck after the coagulating agent is injected into the aneurysm sac.

5. The treatment device of claim 1 wherein the fan portion in the occluding configuration is configured to completely occlude the aneurysm neck.

6. The treatment device of claim 1 further comprising:
    a trigger mechanism for introducing the coagulating agent into the agent channel;
    wherein the agent channel comprises a proximal end in communication with the trigger mechanism to receive the coagulating agent into the agent channel and a distal end in communication with the channel orifice; and
    wherein the agent channel delivers the coagulating agent from the proximal end to the distal end and through the channel orifice into the sac of the aneurysm.

7. The treatment device of claim 6 wherein the channel orifice is an opening in the distal end of the agent channel.

8. A method for treating an aneurysm, the method comprising:
- providing a treatment device comprising a fan portion expandable from a collapsed configuration, a channel orifice defining an opening in the fan portion, and an agent channel,
- the fan portion comprising elongated supports each comprising a first end positioned approximate the channel orifice and a second end opposite the first end and positioned in a distal direction in relation to the channel orifice when the fan portion is in the collapsed configuration;
- joining the agent channel to communicate with the channel orifice when the fan portion is in the collapsed configuration;
- delivering the treatment device to an aneurysm treatment site;
- expanding the fan portion to an occluding configuration approximate a center of an aneurysm neck by moving the second end of each elongated support radially outward toward an interior wall of the aneurysm from a respective initial position in a distal direction in relation to the channel orifice, wherein the expanded fan portion occludes at least a portion of the aneurysm neck and wherein the second end of the elongated support is configured to be in contact with the interior wall of the aneurysm proximate to the neck of the aneurysm;
- injecting a coagulating agent through the agent channel and the channel orifice into the aneurysm sac to coagulate blood present in the aneurysm; and
- collapsing the treatment device from the occluding configuration to an extraction configuration for extraction of the device after the injection of the coagulating agent.

9. The method of claim 8 wherein the step of expanding the fan portion to an occluding configuration approximate a center of an aneurysm neck further comprises the step of creating a barrier between a blood vessel and the aneurysm to prevent the coagulating agent from entering the blood vessel.

10. The method of claim 8 further comprising the step of removing the treatment device through a retrieval catheter.

11. The method of claim 8 further comprising the step of removing the treatment device through a retrieval deployment system.

12. The method of claim 8 further comprising the steps of:
- providing a trigger mechanism; and
- triggering the delivery of the agent by activating the trigger mechanism at a proximal end of the agent channel to deliver the agent from the proximal end of the agent channel to a distal end of the agent channel.

* * * * *